(12) United States Patent
Granlund et al.

(10) Patent No.: US 10,631,761 B2
(45) Date of Patent: Apr. 28, 2020

(54) SYNTHETIC CARDIAC OUTPUT POWER PARAMETER

(71) Applicant: Polar Electro Oy, Kempele (FI)

(72) Inventors: Tommy Granlund, Kokkola (FI); Jussi Peltonen, Jyväskylä (FI); Harri Määttä, Kempele (FI); Juho Rahko, Oulu (FI); Ville Peltola, Oulu (FI)

(73) Assignee: Polar Electro Oy, Kempele (FI)

( * ) Notice: Subject to any disclaimer, the term of this patent is extended or adjusted under 35 U.S.C. 154(b) by 185 days.

(21) Appl. No.: 15/867,225

(22) Filed: Jan. 10, 2018

(65) Prior Publication Data

US 2019/0209049 A1 Jul. 11, 2019

(51) Int. Cl.
*A61B 5/04* (2006.01)
*A61B 5/11* (2006.01)
(Continued)

(52) U.S. Cl.
CPC ............ *A61B 5/1118* (2013.01); *A61B 5/002* (2013.01); *A61B 5/0205* (2013.01); *A61B 5/029* (2013.01); *A61B 5/02028* (2013.01); *A61B 5/02427* (2013.01); *A61B 5/02438* (2013.01); *A61B 5/0404* (2013.01); *A61B 5/1122* (2013.01); *A61B 5/1123* (2013.01); *A61B 5/4866* (2013.01); *A61B 5/681* (2013.01); *A61B 5/7264* (2013.01); *A61B 5/7278* (2013.01); *A61B 5/024* (2013.01); *A61B 5/0464* (2013.01); *A61B 2503/10* (2013.01); *A61B 2505/09* (2013.01); *A61B 2560/0257* (2013.01); *A61B 2562/0219* (2013.01)

(58) Field of Classification Search
CPC ... A61B 5/1122; A61B 5/4866; A61B 5/0464; A61B 5/002; A61B 5/02028; A61B 5/02427; A61B 5/02438; A61B 5/0404; A61B 5/1123; A61B 5/681; A61B 2503/10; A61B 2505/09; A61B 2560/0257; A61B 2562/0219
See application file for complete search history.

(56) References Cited

U.S. PATENT DOCUMENTS

| | | | |
|---|---|---|---|
| 2014/0031703 A1 | 1/2014 | Rayner et al. | |
| 2014/0278220 A1 | 9/2014 | Yuen | |
| 2017/0143262 A1* | 5/2017 | Kurunmaki | .......... A61B 5/0255 |

FOREIGN PATENT DOCUMENTS

| | | |
|---|---|---|
| EP | 2 705 791 A1 | 3/2014 |
| EP | 3 175 782 A1 | 6/2017 |
| WO | 2016/069082 A1 | 5/2016 |

OTHER PUBLICATIONS

Extended European Search Report received for European Patent Application Serial No. 19150283.0 dated May 20, 2019, 7 pages.

* cited by examiner

*Primary Examiner* — Mallika D Fairchild
(74) *Attorney, Agent, or Firm* — FisherBroyles, LLP

(57) ABSTRACT

A method and an apparatus for performing the method are disclosed. The method includes obtaining cardiac output power data on a user; obtaining kinetic data characterizing physical exercise intensity of the physical exercise performed by the user; detecting that a measured cardiac output power exceeds a first threshold or that physical exercise intensity changes according to a rate exceeding a second threshold; upon the detecting, determining a synthetic cardiac output power parameter based at least partly on the kinetic data; and outputting the synthetic cardiac output power parameter.

19 Claims, 11 Drawing Sheets

(51) Int. Cl.
*A61B 5/00* (2006.01)
*A61B 5/029* (2006.01)
*A61B 5/0205* (2006.01)
*A61B 5/02* (2006.01)
*A61B 5/024* (2006.01)
*A61B 5/0404* (2006.01)
*A61B 5/0464* (2006.01)

SYNTHETIC CARDIAC OUTPUT POWER PARAMETER

BACKGROUND

Field

The present invention relates to monitoring physical exercise performance. More particularly, the present invention relates to monitoring cardiac output power of a user.

Description of the Related Art

Presently, cardiac activity values of a user are measured to monitor performance of the user. For example, such monitoring may help the user to train more effectively. However, measured cardiac activity values may be used to make false determination about performance of the user. For example, the user may have trained harder than the measured cardiac activity values indicate. Hence, it may be possible that the user trains too much and does not get enough rest. Therefore, it may be beneficial to provide solutions which provide even more versatile physical exercise monitoring options.

SUMMARY

According to an aspect, there is provided a method for monitoring physical exercise performance, which includes obtaining, by utilizing measurements performed by one or more cardiac activity sensors, cardiac output power data on a user; obtaining, by utilizing measurements performed by one or more sensors, kinetic data characterizing physical exercise intensity of the physical exercise performed by the user; detecting that a measured cardiac output power exceeds a first threshold or that physical exercise intensity changes according to a rate exceeding a second threshold; upon the detecting, determining a synthetic cardiac output power parameter based at least partly on the kinetic data; and outputting the synthetic cardiac output power parameter.

According to another aspect, there is provided an apparatus for monitoring physical exercise performance, which includes at least one processor; and at least one memory including a computer program code, wherein the at least one memory and the computer program code are configured, with the at least one processor, to cause the apparatus to perform operations including obtaining, by utilizing measurements performed by one or more cardiac activity sensors, cardiac output power data on a user; obtaining, by utilizing measurements performed by one or more sensors, kinetic data characterizing physical exercise intensity of the physical exercise performed by the user; detecting that a measured cardiac output power exceeds a first threshold or that physical exercise intensity changes according to a rate exceeding a second threshold; upon the detecting, determining a synthetic cardiac output power parameter based at least partly on the kinetic data; and outputting the synthetic cardiac output power parameter.

According to yet another aspect, there is provided a computer program product embodied on a distribution medium readable by a computer and including program instructions which, when executed by an apparatus, cause the apparatus at least to perform a method including obtaining, by utilizing measurements performed by one or more cardiac activity sensors, cardiac output power data on a user; obtaining, by utilizing measurements performed by one or more sensors, kinetic data characterizing physical exercise intensity of the physical exercise performed by the user; detecting that a measured cardiac output power exceeds a first threshold or that physical exercise intensity changes according to a rate exceeding a second threshold; upon the detecting, determining a synthetic cardiac output power parameter based at least partly on the kinetic data; and outputting the synthetic cardiac output power parameter.

Some embodiments are described in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following some examples will be described in greater detail with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
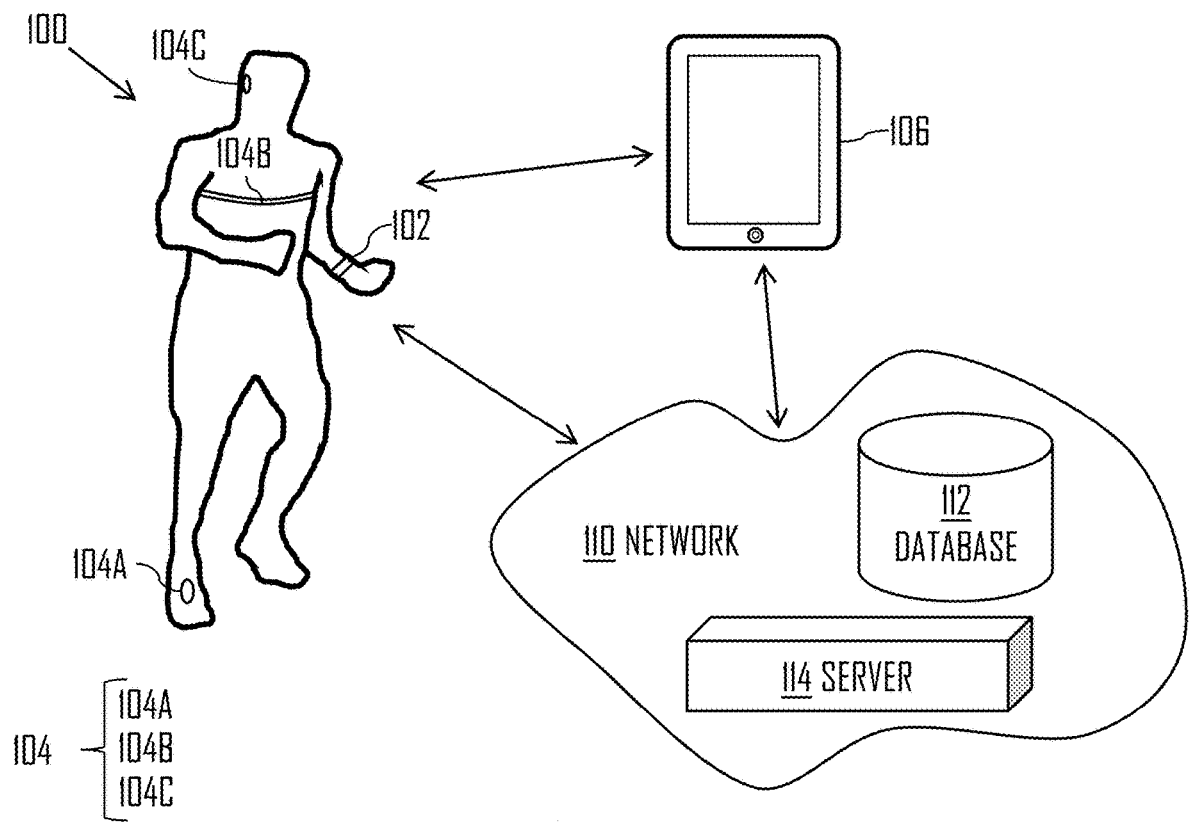
FIG. 1 shows a physical exercise monitoring system to which the embodiments may be applied.

FIG. 1 illustrates a physical exercise monitoring system to which embodiments of the invention may be applied. Said system may be used to monitor physical training, activity, and/or inactivity of a user 100. Thus, the embodiments may not be limited to monitoring and/or measuring physical training/exercise of the user 100, and thus said system may be used to monitor physical activity and/or inactivity during the day and/or night (e.g. 24 hours a day). Such may be possible using one or more devices described with respect to FIG. 1 and in the embodiments below.

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices. I.e. the embodiments may not necessarily be limited to wrist device or devices 102.

The wrist device 102 may be, for example, a smart watch, a smart device, sports watch, and/or an activity tracking apparatus (e.g. bracelet, arm band, wrist band, mobile phone). The wrist device 102 may be used to monitor physical activity and/or performance of the user 100 by using data from internal sensor(s) comprised in the wrist device 102, data from external sensor device(s) 104A-C (or simply sensors 104 including one or more of said external sensors 104A-C), and/or data from external services (e.g. training database 112). It may be possible to receive physical activity related information from a network 110, as the network may comprise, for example, physical activity related information on the user 100 and/or some other user(s). Thus, the wrist device 102 may be used to monitor physical activity related information one the user 100 and/or the other user(s). Naturally, one or more of the external sensor device(s) 104 may be worn by the other user(s), and thus information received from said one or more sensor device(s) 104 may be monitored from the wrist device 102 by the user 100. The network 110 may comprise the training database 112 and/or the server 114. The server 114 may be configured to enable data transfer between the training database 112 and some external device, such as the wearable device (e.g. wrist device 102). Hence, the database 112 may be used to store cardiac activity measurement data (sometimes referred to as cardiac output power data), for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN), ANT/ANT+, and/or Near Field Communication (NFC), may also be used.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating with the cellular network. It is also pointed out that, in general, the wearable device may comprise a communication circuitry capable of cellular, Bluetooth, NFC, WLAN, and/or LAN communication.

The wrist device 102 may be used to monitor activity and/or inactivity of the user 100. Similarly, the portable electronic device 106 may be used to monitor the activity and/or inactivity of the user 100. Such may require the portable electronic device 106 to acquire physical activity related data from the wrist device 102, some other wearable device, and/or from external sensor device(s) 104A-C. However, it may be that the portable electronic device 106 determines activity and/or inactivity of the user 100 by utilizing internal sensor(s), such as accelerometer or satellite positioning circuitry.

The system may comprise a cardiac activity circuitry configured to measure, obtain and/or determine cardiac output power of the user 100, such as heart rate, Heart Beat Interval (HBI) and/or Heart Rate Variability (HRV), for example. For example, the cardiac activity circuitry may comprise a processing unit for obtaining one or more cardiac output power measurements and determine the cardiac output power based on said measurements (e.g. heart beat samples). However, the processing unit may not be necessary in all implementations. Such cardiac activity circuitry may be comprised in the sensor(s) 104 (e.g. head sensor, torso sensor, such as heart rate transmitter) and/or in the wrist device 102.

The cardiac activity circuitry may comprise an optical cardiac activity sensor unit configured to measure the cardiac activity of the user 100. Example of such sensor may be a PPG (photo plethysmography) sensor. The optical cardiac activity sensor unit may detect the cardiac output power of the user 100 by optical measurement, which may comprise emitting light towards body tissue of the user 100 and measuring the bounced, reflected, scattered and/or emitted light from the body tissue of the user 100. The emitted light may alter when travelling through veins of the user 100 and the alterations may be detected by the optical cardiac activity sensor unit. By using the detected data, the cardiac activity circuitry, may output a cardiac output power indicator or parameter, such as heart rate, HRV and/or HBI for example. The optical cardiac activity sensor unit may obtain via the measurement a cardiac activity signal characterizing or carrying the cardiac activity information on the user.

Alternatively or additionally, the cardiac activity circuitry may comprise biosignal and/or electrode based sensor(s) for measuring cardiac output power of the user. In short, the cardiac output power of the user may be measured using one or more techniques using one or more sensors in one or more devices. It is also possible to use measurements from two or more sensor using one or more techniques to obtain the cardiac output power of the user.

It also noted that the cardiac activity circuitry may produce raw measurement data of the cardiac activity and/or it may process the measurement data into cardiac output power information, such as heart rate for example. The sensor(s) in the cardiac activity circuitry may comprise data processing capabilities. Also, the wrist device 102 and/or some other wearable device may comprise a processing circuitry configured to obtain the cardiac output power data from the cardiac activity circuitry and to process said data into cardiac output power information, such as a cardiac output power metric characterizing the cardiac output power of the user 100. For example, the measurement data provided by the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, and/or a polarization blood flow sensor.

In addition to obtaining cardiac output power data (sometimes referred to as cardiac activity data) on the user, the system may comprise one or more sensors for measuring motion of the user. Such sensors may comprise accelerometer(s), gyroscope(s), magnetometer(s), satellite positioning circuitry or circuitries, altimeter, and/or barometer, to name a few examples. For example, the system may obtain kinetic data (sometimes referred to as motion data) on the user.

In one example, the system comprises a motion circuitry configured to measure motion induced by the user 100. The motion circuitry may comprise one or more gyroscopes, one or more accelerometers and/or one or more magnetometers. The motion circuitry may use other motion data, such as location data of the user, to determine motion of the user 100. For example, the motion circuitry may comprise a satellite positioning circuitry, such as a global navigation satellite system (GNSS) circuitry. The GNSS circuitry may comprise, for example, a Global Positioning System (GPS) and/or a GLObal NAvigation Satellite System (GLONASS). The satellite positioning circuitry may be used for receiving satellite positioning data. The satellite positioning data may be used, by the wearable device, to determine motion and/or location of the user 100. The motion circuitry may further comprise the altimeter, and/or the barometer.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity or speed data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus for example, the satellite positioning data may also be utilized in the sensor fusion.

The motion circuitry may be used to obtain kinetic data on the user. For example, kinetic data may be used to determine acceleration and/or speed of the user. The motion circuitry, similar to the cardiac activity circuitry, may be comprised in one physical entity (e.g. wrist device 102) or shared between two or more physical entities. For example, the leg sensor 104A may comprise a stride sensor and/or foot pod for measuring cadence of the user during running, walking and/or cycling. It is also noted that the motion circuitry may comprise one or more sensors integrated with equipment, such as gym equipment or bike/cycle/bicycle. For example, the motion circuitry may comprise a power sensor for measuring pedalling power and/or cadence sensor for measuring pedalling cadence, or some other type of power and/or cadence sensor.

Figure 2:
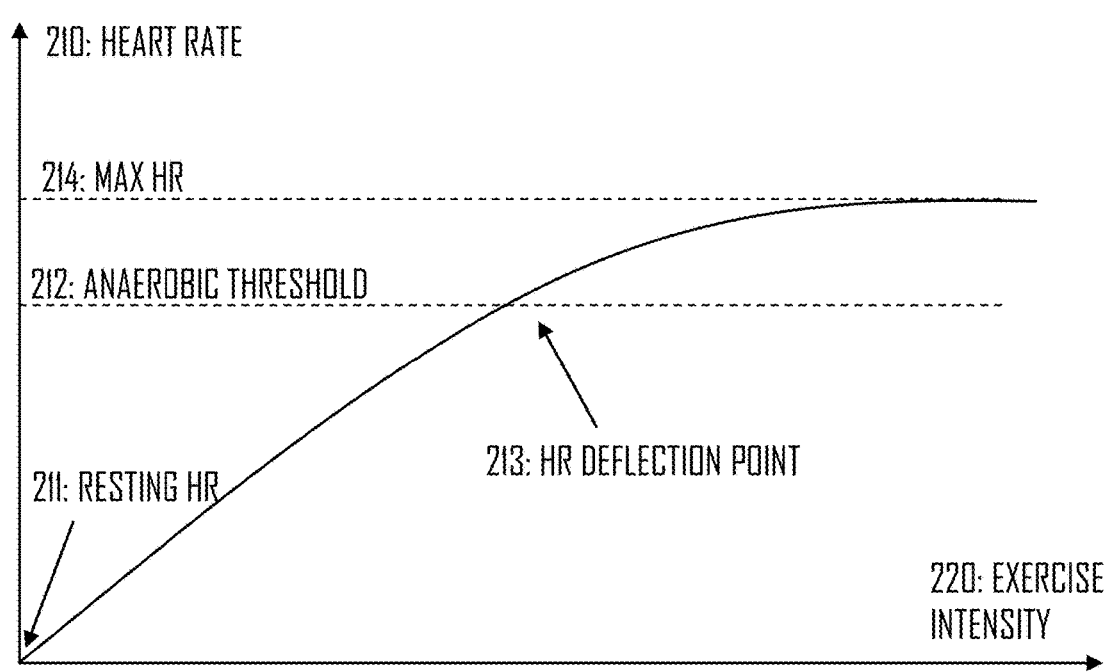
FIG. 2 illustrates relationship between exercise intensity and heart rate according to one example.

Let us then look closer on the example of FIG. 2 in which measured heart rate 210 is illustrated as a function of exercise intensity 220. Heart rate 210 is used as simple example, but it is noted that similar logic may apply to relationship between measured cardiac output power and exercise intensity 220 (i.e. physical exercise intensity). Referring to FIG. 2, a user may have a certain resting heart rate (resting HR) 211, anaerobic threshold 212, and maximum heart rate (max HR) 214. The anaerobic threshold 212 may be associated with a certain heart rate deflection point 213.

User's heart rate 210 may increase substantially linearly with respect to increased exercise intensity 220 between resting heart rate 211 and the heart rate deflection point 213 associated with the anaerobic threshold 212. Between the heart rate deflection point 213 and the maximum heart rate 214 the increase may not be linear, for example. In some cases the relationship between heart rate 210 and exercise intensity 220 is not linear, but may still follow a certain model. Said model may be determined via measurement, for example, and may be different between users. However, it may still be that heart rate 210 rises with a lower slope or angular coefficient once the anaerobic threshold 212 is reached even though exercise intensity 220 continues to increase or rise. Eventually, if the exercise intensity 220 further increases, the heart rate 210 reaches maximum heart rate 214. However, it may still be that the exercise intensity 220 continues to increase. For example, the user may continue running on a certain speed for some time period even though his/her max HR 214 is obtained. On the other hand, if exercise intensity rapidly changes (e.g. user stops or accelerates), heart rate 210 measurement may lag behind as it may require heart rate samples from a longer time period. Hence, effect of such rapid changes in exercise intensity may totally or at least partially be lost by using simple heart rate 210 measurement.

Hence, it is noted that using measured heart rate as a tool for monitoring physical exercise performance may have its weaknesses. That is, measured heart rate may not reflect exercise intensity in adequate manner in some scenarios. Therefore, it may be beneficial to provide solutions which provide even more accurate monitoring parameters for the user in order to make his/her training more reasonable, e.g. reduce overtraining.

Figure 3A:
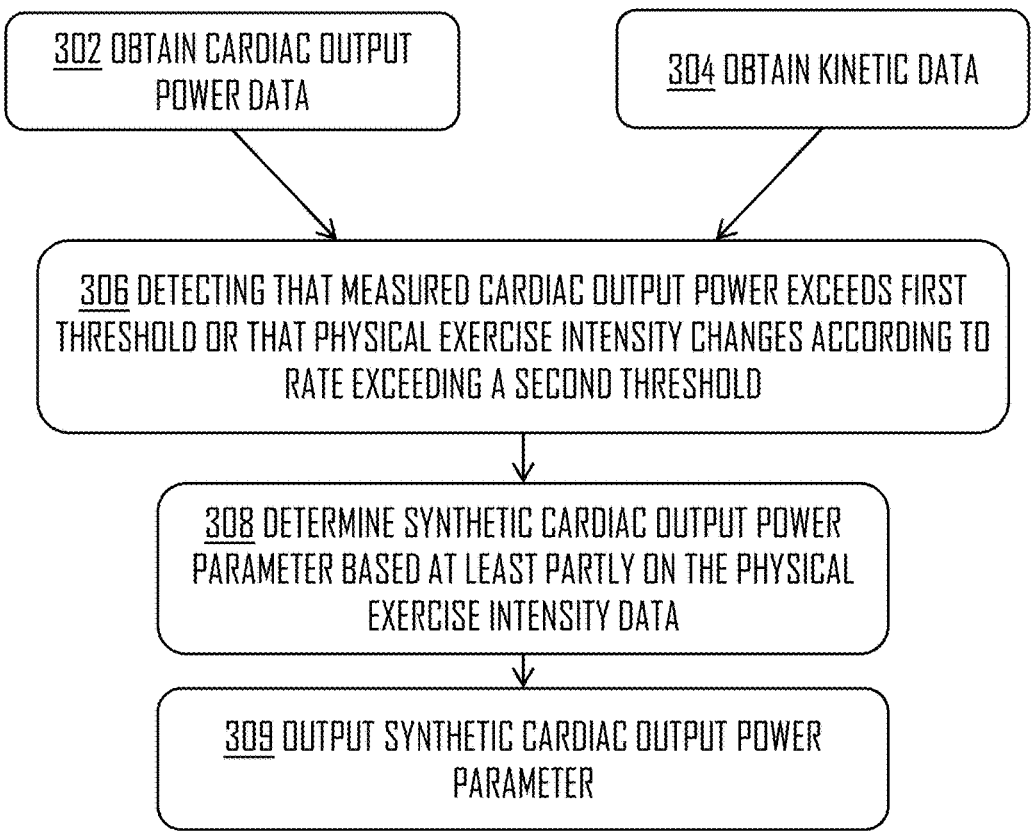
FIG. 3A illustrates a flow diagram according to an embodiment.

FIG. 3A illustrates a flow diagram of a method according to an embodiment. Referring to FIG. 3A, the method for monitoring physical exercise performance comprises: obtaining (block 302), by utilizing measurements performed by one or more cardiac activity sensors, cardiac output power data on a user; obtaining (block 304), by utilizing measurements performed by one or more sensors, kinetic data characterizing physical exercise intensity of the physical exercise performed by the user; detecting (block 306) that a measured cardiac output power exceeds a first threshold or that physical exercise intensity changes according to a rate exceeding a second threshold; upon said detecting, determining (block 308) a synthetic cardiac output power parameter based at least partly on the kinetic data; and outputting (block 309) the synthetic cardiac output power parameter.

According to an embodiment, the measuring and obtaining the cardiac output power data and the kinetic data is performed continuously, and the determined synthetic output power parameter outputted in real-time during the continuous measuring and/or obtaining the cardiac output power data and the kinetic data.

The one or more cardiac activity sensors may be comprised in the cardiac activity circuitry discussed above. The one or more sensors (e.g. motion sensors) used to measure kinetic data may be comprised in the motion circuitry discussed above. Said method may be performed, for example, in the server computer 114, the wearable device (e.g. wrist device 102) and/or the portable electronic device 106. In some embodiments, different method steps are performed by different entities of the system described with respect to FIG. 1. For example, measuring the cardiac output power and kinetic data may be performed by the wrist device 102 and/or the sensor(s) 104 and the calculation of the synthetic cardiac output power parameter may be performed by the server computer 114. However, it is also possible that all steps are performed by the wearable device, for example.

Figure 3B:
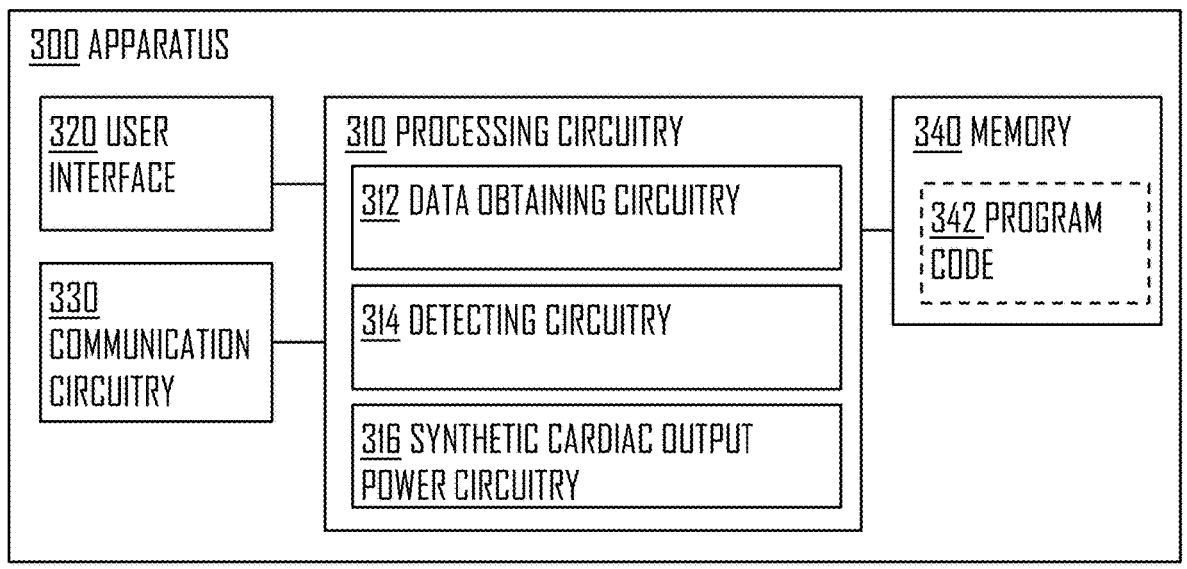
FIG. 3B illustrates an apparatus according to an embodiment.

FIG. 3B illustrates one example embodiment of apparatus 300 for performing the method of FIG. 3A. As discussed, the apparatus 300 may be or be comprised in the server computer 114, the wrist device 102 (or more broadly: the wearable device) and/or portable electronic device 106, or functionalities of the apparatus 300 may be shared between different elements of the system. The apparatus 300 may comprise sensors, such as the cardiac activity circuitry and/or motion circuitry. However, these may also be comprised in different devices communicatively coupled with the apparatus 300.

Referring to FIG. 3B, the apparatus 300 comprises processing circuitry 310, such as at least one processor, and at least one memory 340, including a computer program code (software) 342, wherein the at least one memory 340 and the computer program code (software) 342, are configured, with the at least one processor, to cause the respective apparatus 300 to carry out any one of the embodiments describe above and hereinafter. For example, said embodiments comprise steps of FIG. 3A.

The memory 340 may be implemented using any suitable data storage technology, such as semiconductor based memory devices, flash memory, magnetic memory devices and systems, optical memory devices and systems, fixed memory and removable memory. The memory 340 may additionally or alternatively be used to store information, such as cardiac output power data and/or kinetic data on the user, and/or data derivable from said cardiac output power data and/or kinetic data.

The apparatus 300 may further comprise a communication circuitry 330 comprising hardware and/or software for realizing communication connectivity according to one or more communication protocols. The communication circuitry 330 may provide the apparatus 300 with communication capabilities to exchange data between devices. The communication circuitry 330 may enable wireless and/or wired connection to other devices of the system. The wireless communication circuitry 330 may be based on Bluetooth protocol, e.g. Bluetooth Low Energy, NFC technology, wherein the NFC technology may enable data transfer on short distances, and/or WLAN. However, the wireless communication circuitry 330 may not be limited to these technologies, and thus, for example, cellular communication link, or similar, may also be provided by the communication circuitry 330, providing the apparatus 300 a long range communication capability. For example, the communication circuitry 330 may be used to receive cardiac output power data and/or kinetic data from one or more sensors that are external to the apparatus 300 and/or from the database 112.

The apparatus 300 may also comprise user interface 320 comprising, for example, at least one keypad, a microphone, a touch display, a display, a haptic element and/or a speaker. The user interface 320 may be used to control the respective apparatus 300 by the user 100. For example, the user interface 320 may be used to output the synthetic cardiac output power parameter to the user. Hence, the user 100 may adjust his/her training accordingly. Outputting may be performed via display (visual indicator), speaker (e.g. audible indicator) and/or haptic element (e.g. haptic feedback). The outputting, e.g. display, audio and/or haptic output, may be performed in real-time which may mean that the outputting is performed during measuring and/or when user is performing the physical activity, such as sports (e.g. running, swimming, or jogging). The user interface 320 may be used to output any other data or indication based on the data to the user, such as kinetic data output, power data output, and/or speed data output.

According to an embodiment, the processing circuitry 310 comprises a data obtaining circuitry 312, a detecting circuitry 314, and a synthetic cardiac output power circuitry 316. The circuitry 312 may be configured to perform operations described with respect to block 302 and 304. The circuitry 314 may be configured to perform operations described with respect to block 306. The circuitry 316 may be configured to perform operations described with respect to block 308 and 309.

Regarding block 309, i.e. outputting the synthetic cardiac output power parameter may comprise displaying the parameter to the user, storing the parameter into a database (e.g. database 112), and/or using the parameter in calculation of some other parameter(s). For example, said parameter may be used to calculate training load, energy consumption estimate, and/or training effect of the user. I.e. the synthetic cardiac output power parameter may be used as an input value in calculating said training load, energy consumption estimate, and/or training effect. Training load, energy consumption estimate, and/or training effect may be outputted by the apparatus 300, for example.

Figure 4A:
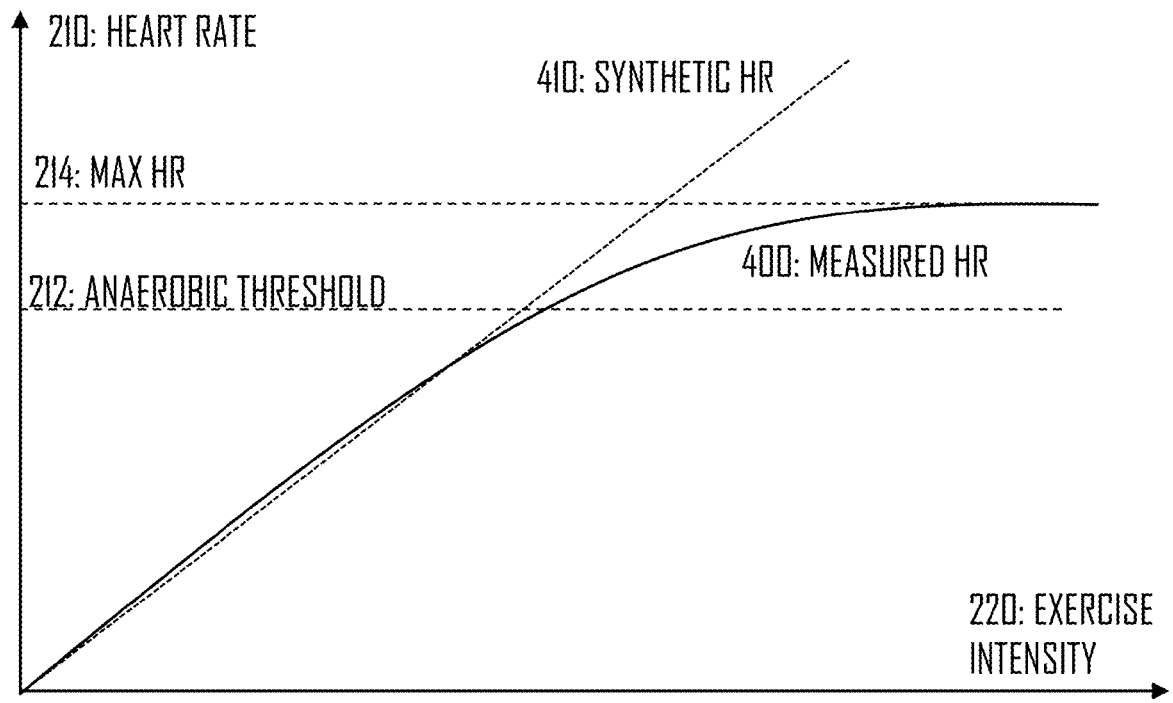
FIGS. 4A, 4B, and 4C illustrate some embodiments.
Figure 4B:
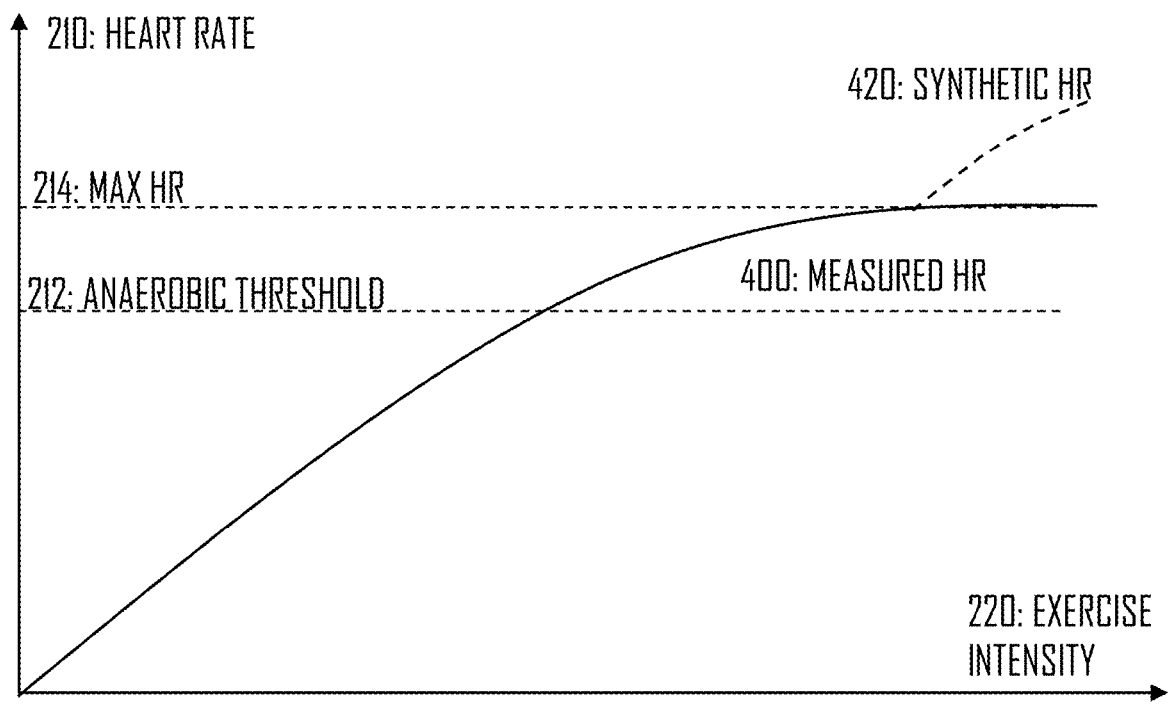
Figure 4C:
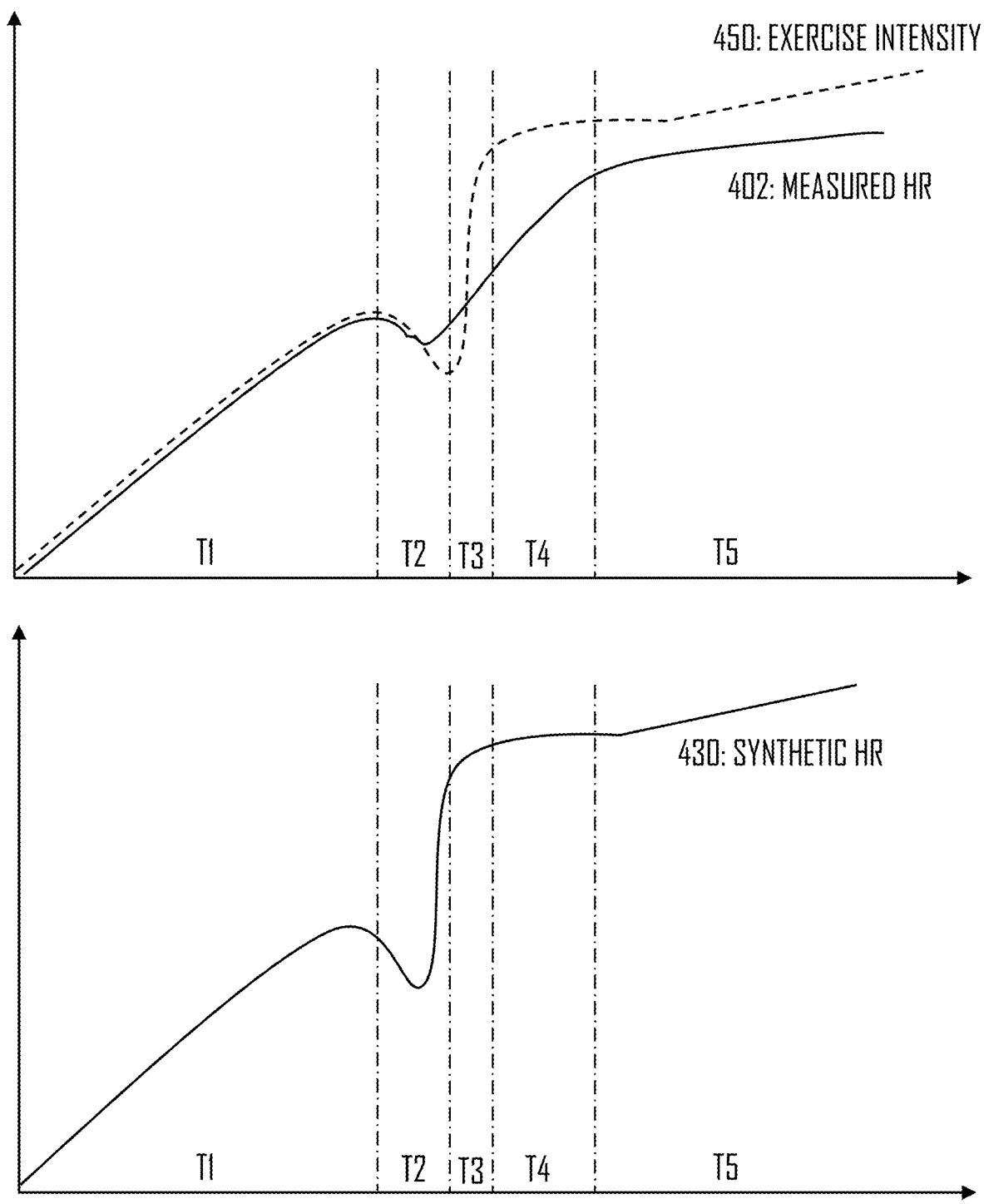

Let us then look closer on some example embodiments of FIGS. 4A, 4B, and 4C. Referring first to FIG. 4A, measured heart rate 400 is illustrated together with synthetic heart rate 410 (dotted line). Again, heart rate is used as one example of cardiac output power parameter which may comprise other parameters than heart rate. The measured heart rate curve 400 may act similarly as shown earlier in FIG. 2. However, according to the proposed solution, the synthetic heart rate 410 may act differently compared with the measured heart rate 400 on values that exceed the anaerobic threshold (e.g. the first threshold). So, FIG. 4A may illustrate one example embodiment on how the synthetic cardiac output power parameter may be determined based on kinetic data. That is, kinetic data may represent exercise intensity 220 and/or may be used to determine exercise intensity 220. Hence, according to an embodiment, the synthetic heart rate 410 substantially linearly corresponds to the exercise intensity 220. So, the synthetic heart rate 410 may be determined based on the exercise intensity, such as based on the kinetic data.

Referring to FIG. 4B showing another example embodiment, synthetic heart rate 420 may be determined in response to determining that the measured heart rate 400 is substantially equal to or over determined maximum heart rate 214 of the user. As shown in FIG. 4B, the correspondence between the synthetic heart rate 420 and exercise intensity 220 is not necessarily linear. Similar note is made with respect the example of FIG. 4A.

Referring to FIG. 4C, exercise intensity 450 (dotted curve) is shown together with measured heart rate 402 during time periods T1, T2, T3, T4, and T5. As shown, the measured heart rate 402 may represent exercise intensity 450 in a quite accurate manner during period T1 and substantially during period T2. However, during periods T3, T4, and T5 the correspondence is not that good. There are at least two different aspects which may be highlighted. Firstly, during period T5, the measured heart rate 402 may be over the anaerobic threshold, and thus the measured heart rate may not represent the exercise intensity 450 in an accurate manner. Secondly, during T2 and especially T3, exercise intensity 450 rapidly changes, and the measured heart rate lags behind. The lagging continues during T4.

Hence, it may be beneficial to utilize synthetic heart rate 430 (again an example of synthetic cardiac output power parameter) to better represent the exercise intensity 450. For example, the apparatus may detect during periods T2 and/or T3 that the exercise intensity changes according to a rate exceeding a threshold (e.g. faster than the threshold), and thus may trigger determination of the synthetic heart rate based at least partly on the kinetic data. The change rate of the exercise intensity may be determined based on the kinetic data and/or measured heart rate 402 or some other measured cardiac output power parameter. For example, if speed of the user exceeds a threshold or acceleration of the user exceeds a threshold, the apparatus 300 may trigger the synthetic cardiac output power parameter determination based at least partly on the kinetic data. So, according to an embodiment, the apparatus 300 may determine, based on kinetic data, that the exercise intensity changes according to a rate exceeding a threshold, and in response trigger the synthetic cardiac output power parameter determination based at least partly on the kinetic data. So, for example, if acceleration represents exercise intensity, the synthetic cardiac output power parameter may be determined based at least partly on acceleration.

It is noted that the triggering of determination of the synthetic heart rate based at least partly on the kinetic data may refer to determination based on solely kinetic data, based on kinetic data and the measured cardiac output power data, based on determining some other data/parameter (such as power and/or speed based on the kinetic data) or based on said determined some other data/parameter and the measured cardiac output power, for example.

According to an embodiment with reference to FIGS. 4A, 4B, and 4C, the apparatus 300 determines the synthetic cardiac output power parameter (e.g. 410, 420) based on the cardiac output power data (e.g. measured data, such as measured heart rate 400) before the detecting that the measured cardiac output power exceeds the first threshold (e.g. anaerobic threshold 212 or maximum heart rate 214) or that the physical exercise intensity changes according to a rate exceeding the second threshold. This may mean that the synthetic cardiac output power parameter is determined only based on the measured cardiac output power and/or directly is or equals to the measured cardiac output power. For example, during T1 the synthetic heart rate 430 may be determined based on the measured heart rate 402. For example, the synthetic heart rate 430 be equal to the measured values during T1. However, during T2 and T3, the synthetic heart rate may additionally or alternatively be determined at least partly based on the kinetic data as exercise intensity 450 changes at a rate exceeding the second threshold. During T4 and T5, the synthetic heart rate may additionally or alternatively be determined at least partly based on the kinetic data as measured heart rate 402 exceeds the first threshold (first threshold not shown in FIG. 4C, but may be based on the max HR or anaerobic threshold, for example).

According to an embodiment, the first threshold is at heart rate value corresponding to aerobic threshold of the user 100. As for maximum heart rate 214 and anaerobic threshold 212, the aerobic threshold may be determined based on predetermined model and user characteristics (e.g. user age and gender), and/or performing one or more physiological tests on the user 100.

According to an embodiment, the first threshold substantially equals to a cardiac output power value corresponding to the anaerobic threshold 212 of the user.

According to an embodiment, the first threshold substantially equals to a cardiac output power value corresponding to the maximum heart rate 214 of the user.

According to an embodiment, the cardiac output power represents or indicates a heart rate parameter. As described earlier, heart rate is used one example of cardiac output power. However, other parameters, such as HRV and/or HBI, may be utilized.

According to an embodiment, the cardiac output power represents or indicates two or more heart rate parameters. For example, heart rate and HRV.

According to an embodiment and with reference to FIGS. 4A and 4B, the outputted synthetic cardiac output power parameter (e.g. synthetic HR 410, 420) indicates a value that is greater than the maximum heart rate 214 of the user. I.e. the synthetic cardiac output power parameter may be configured to indicate values that are greater than the maximum heart rate 214.

In general, the outputted synthetic cardiac output power parameter may indicate heart rate values, percentage of maximum heart rate 214, percentage of heart rate corresponding to the anaerobic threshold 212, and/or percentage of heart rate reserve (HRR), for example. HRR is the difference between Maximum Heart Rate (HRmax) and Resting Heart Rate (HRrest). So, for example, the outputted synthetic cardiac output power parameter could indicate 125% of maximum heart rate 214 which may mean that the exercise intensity 220 is higher than what is indicated by the measured cardiac output power (e.g. 95% of max heart rate 214). So, the synthetic cardiac output power parameter may represent intensity of the physical exercise using values that are associated or related to the actual cardiac output power of the user. The synthetic cardiac output power parameter may be referred to also as virtual heart rate or a tachometer parameter (or rev counter parameter).

Accordingly, the synthetic cardiac output power parameter may be determined on the basis of measured cardiac output power (e.g. before the first threshold or second threshold is exceeded), on the basis of measured exercise intensity (e.g. using kinetic data), or both the measured cardiac output power and the measured exercise intensity. For example, initial estimation may be acquired using the measured cardiac output power which may further be made more accurate using additional information, such as plain kinetic data, or derivable of the kinetic data, such as power data or speed data.

According to an embodiment, the synthetic cardiac output power parameter (e.g. synthetic HR 410, 420) indicates a value that is greater than the measured heart rate of the user.

According to one example embodiment, the synthetic cardiac output power parameter indicates values exceeding the maximum heart rate of the user in response to the measured heart rate of the user being at the maximum heart rate for a certain time. That is, the apparatus 300 may detect that the heart rate is at maximum level and trigger time measurement. The synthetic cardiac output power parameter may then be further based on the time measurement, i.e. the longer the heart rate is at maximum or at least within certain range from maximum (e.g. within 5 or 10% of maximum), the higher values the synthetic cardiac output power parameter may indicate. In this example, the exercise intensity may increase as the heart rate of the user is at maximum for a certain time. So, the synthetic cardiac output power parameter may continue to rise as long as the user's heart rate is at the maximum or within said range. As the measured heart rate starts to decrease, so may the values indicated by the synthetic cardiac output power parameter. However, the decreasing of the synthetic cardiac output power parameter may happen, for example, with substantially same or smaller angular coefficient as the actual measured heart rate. Hence, the synthetic cardiac output power parameter may continue to indicate values which exceed the maximum heart rate for some time although user's heart rate would have dropped, for example, 30% from maximum.

Figure 5:
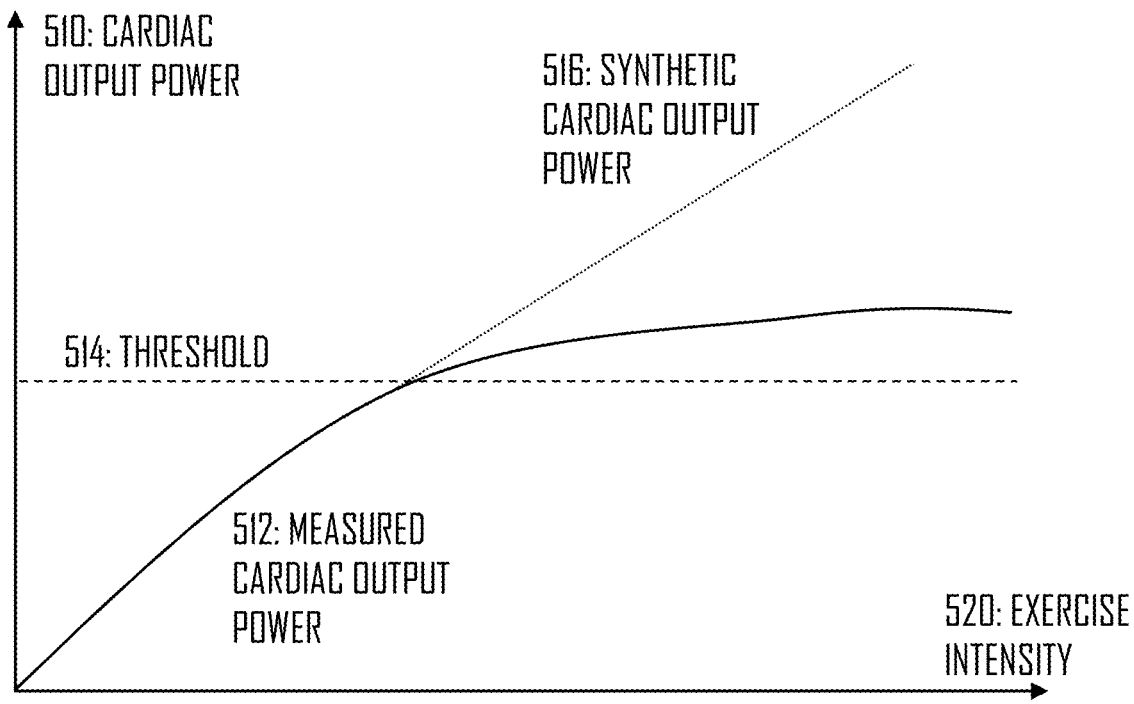
FIG. 5 illustrates an embodiment.

FIG. 5 illustrates an embodiment. Scale for cardiac output power 510 is shown on left side and scale for exercise intensity 520 is shown on right side of the Figure. FIG. 5 shows relationship cardiac output power 510 as a function of exercise intensity 520. Referring to FIG. 5, measured or real cardiac output power 512 of the user is indicated with respect to exercise intensity 520 of the user (e.g. measured exercise intensity). As with previous examples, as exercise intensity 520 increases (e.g. speed increases, acceleration increases, angle of slope increases (and user is moving with a certain speed uphill), and/or power output increases) the measured cardiac output power 512 eventually saturates as it may not exceed maximum heart rate limit of the user. Therefore, the proposed solution triggers determination of synthetic cardiac output power 516 when or in response to exceeding the threshold 514 (e.g. max heart rate, aerobic threshold, anaerobic threshold). The determination of the synthetic cardiac output power 516 may be based at least partly on the measured exercise intensity which may be based on kinetic data and/or predetermined relationship between exercise intensity 520 and cardiac output power 510, for example. For example, the synthetic cardiac output power determination may assume that the cardiac output power 510 continues to rise with same or similar angular coefficient as before the threshold 514 is exceeded, and thus the synthetic cardiac output power 516 may so indicate. It is noted that, in general, the threshold 514 may relate to heart rate, such as max heart rate, but may be determined based on the exercise intensity data, such as kinetic data. That is, if exercise intensity exceeds a certain threshold, the synthetic cardiac output power determination may be triggered.

Exercise intensity may refer to how much energy is expended when exercising. Perceived intensity may vary between each user. According to an example embodiment, exercise intensity is the amount of physical power (expressed as a percentage of the maximal oxygen consumption) that the body uses when performing an activity. For example, exercise intensity may define how hard the body has to work to walk a mile in 20 minutes. It is noted that conventionally, heart rate may be used as one exercise intensity measurement or used as an indicator of exercise intensity. However, as indicated above, the measured heart rate may not reflect the current exercise intensity, for example, if the first or the second threshold(s) are exceeded. Hence, for example, kinetic data or derivable from kinetic data, such as power output or speed, may be used further to determine the synthetic cardiac output power 516 which may better reflect the current exercise intensity 520.

Figure 6A:
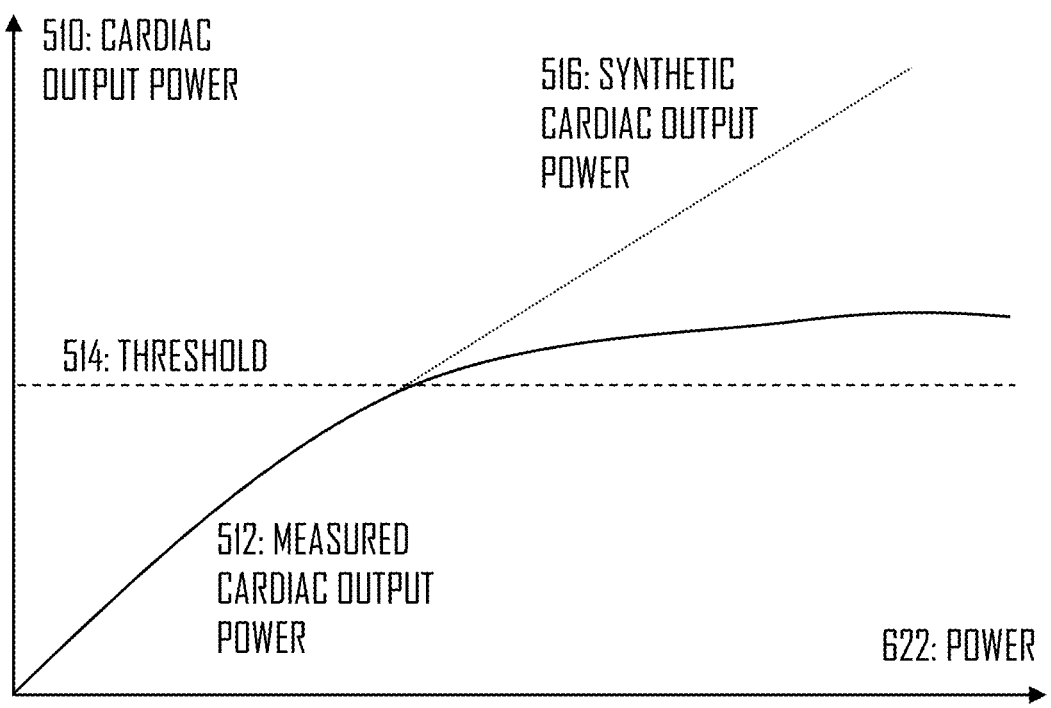
FIGS. 6A, 6B, 6C, 6D, 6E, and 6F illustrate some embodiments.

FIG. 6A illustrates an example embodiment of using power data for determining the synthetic cardiac output power 516. In FIG. 6A, power 622 (e.g. measured power) may be used as one indicator of exercise intensity similarly as in more general terms in FIG. 5 (i.e. exercise intensity 520). That is, the cardiac output power 510 may be indicated as a function of power 622, such as exercise power (e.g. swimming power, running power, or cycling power). Accordingly, the apparatus 300 may obtain physical exercise power data based at least on the kinetic data; and determine the synthetic cardiac output power parameter 516 based at least partly on the physical exercise power data. The use of the power data may be triggered once the first or the second threshold is exceeded. The physical exercise power data and physical exercise power may refer to energy consumed by the user with respect to time unit, i.e. the amount of energy transferred per unit time. There may be different ways to measure physical exercise power. We'll discuss three examples in more detail: swimming power, cycling power (or pedalling power) and running power.

Regarding swimming, swimming power may be obtained by measuring user's swimming speed and using said speed and a predetermined model to determine swimming power. One example may be to measure how much time it takes to swim a pool length, and provide the swimming power estimate based on said pool length time (e.g. 25 meter or 50 meters) and the predetermined model.

Regarding cycling, cycling power may be measured by using specific sensor(s) in bicycle pedal(s). For example, a cycling power meter may use strain gauges to measure torque applied to the pedal(s), and when combined with angular velocity, cycling power may be determined. For example, the sensor(s) may be comprised in the sensor(s) 104 and the power calculation may be performed by apparatus 300.

Figure 6B:
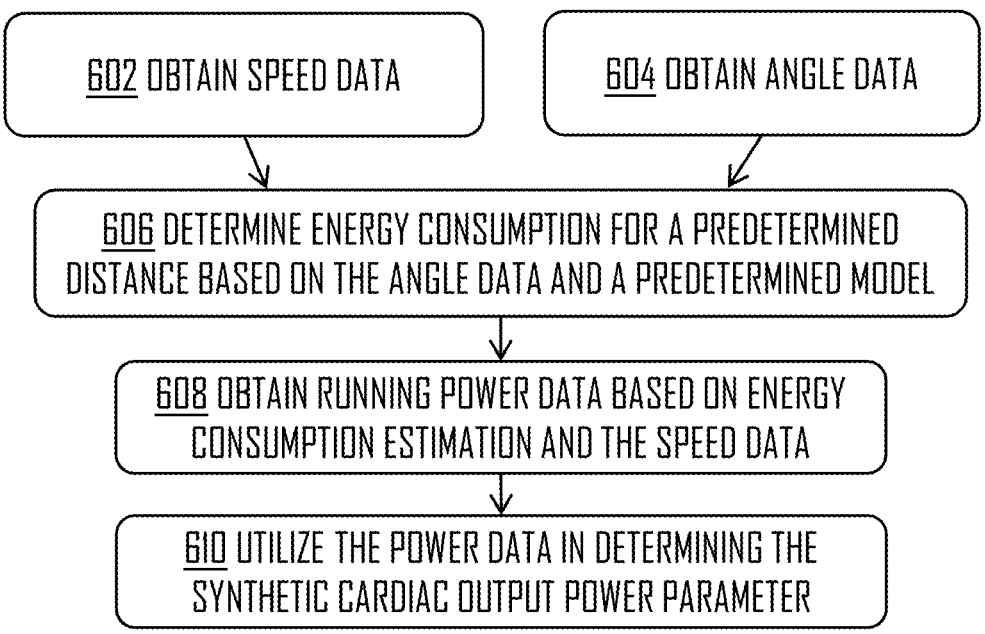

Regarding running power and with reference to FIG. 6B, there is provided a novel method for obtaining and/or determining running power of a user, the method comprising: obtaining speed data (block 602) and angle data (block 604) on a route of the user; obtaining (block 606) an energy consumption estimation for a predetermined distance at least on the basis of a predetermined model and the angle data; and obtaining (block 608) the running power data at least on the basis of the energy consumption estimation and the speed data. The running power data may indicate a running power estimation of the user.

According to an embodiment, the running power data is utilized in determining the synthetic output power parameter by the apparatus 300 (block 610).

The speed data may be measured, for example, using stride sensor(s), foot pod(s), and/or satellite positioning circuitry. In general, the motion circuitry discussed above may be used to measure speed data on the user. The angle data may be discussed later in more detail, but may refer to slope angle data which may be measured using altimeter, barometer, and/or satellite positioning circuitry. That is, the angle data may reveal angel of a slope, for example.

Figure 6C:
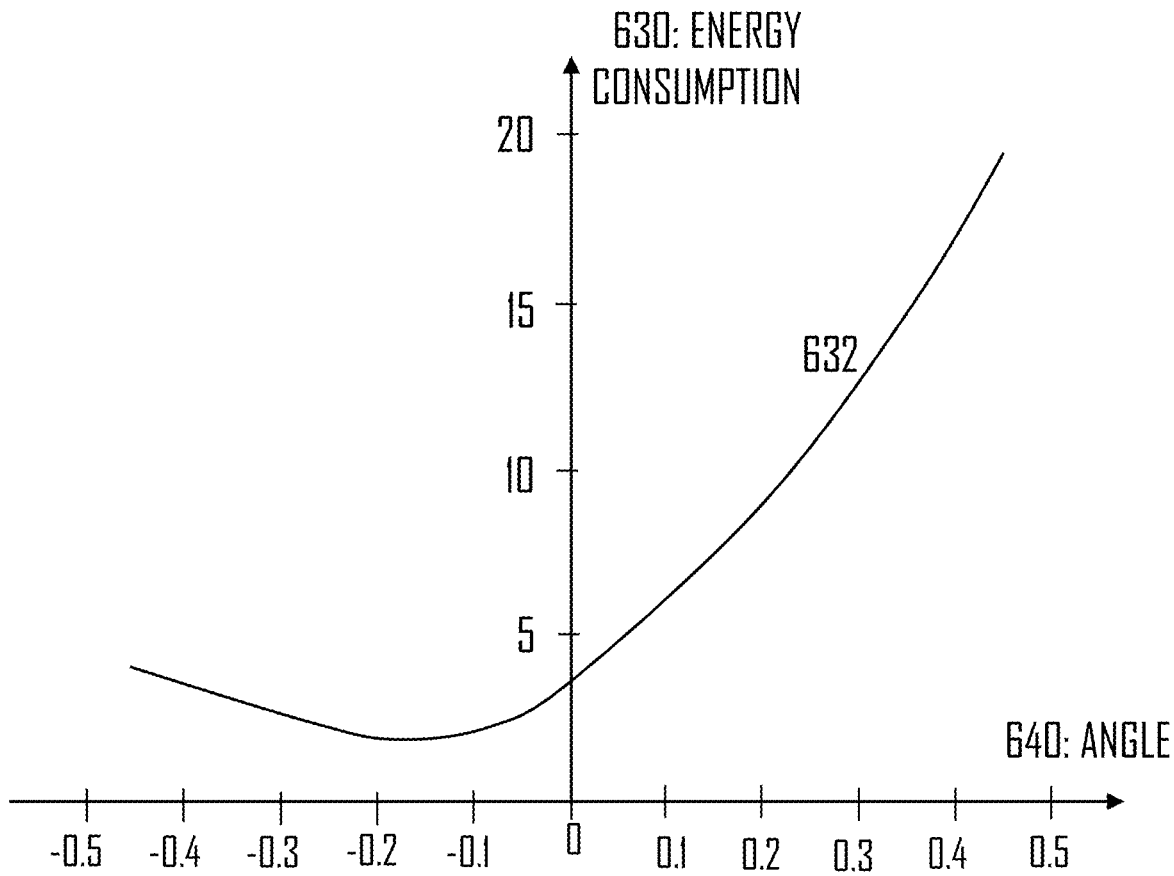

One example of the predetermined model discussed with respect to block 606, may be shown in FIG. 6C illustrating an embodiment. Referring to FIG. 6C, energy consumption 630 and angle 640 may be shown as axis and energy consumption curve 632 is illustrated to indicate correspondence between the energy consumption 630 and the angle 640 (angle of ascent or angle of descent). So, the curve 632 may indicate how much energy is consumed per predetermined distance (e.g. meter) depending on the angle. The angle is indicated in radians. It can be seen in the Figure that as angle of ascent increases, so does the consumed energy. Lowest energy consumption may be situated between −0.2 and −0.1 radians, i.e. angle of descent. However, the correlation is not necessarily linear or direct. For example, the energy consumption 630 may further depend on a correction or change factor.

According to an embodiment, the cost of running may be used to determine energy consumption (also referred to as energy expenditure), wherein cost of running is Joules (J)

per kilograms (kg) per meters (m)), i.e. J/(kgm). I.e. cost of running may indicate how much energy is required to run one meter for a user weighing X kilograms, wherein X is weight of the user. For example, there may be a predetermined correlation between cost of running and energy consumption determined, for example, based on laboratory tests utilizing one or more force plates. For example, it is possible to determine the correlation between the cost of running and running power, and use said correlation in determining the running power. For example, said correlation may be determined in a sports laboratory using suitable equipment.

According to an embodiment, the energy consumption is indicated as cost of walking, wherein cost of walking is Joules (J) per kilograms (kg) per meters (m)), i.e. J/(kgm). In general terms, cost of walking may be less energy consuming compare with cost of running. Cost of walking can be utilized in similar manner as cost of running, e.g. for determining walking power and/or energy consumption.

Figure 6D:
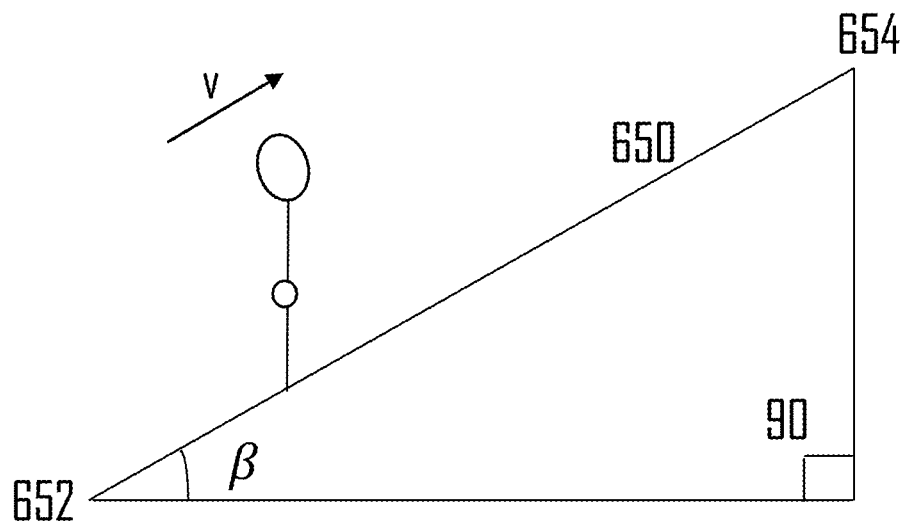
Figure 6E:
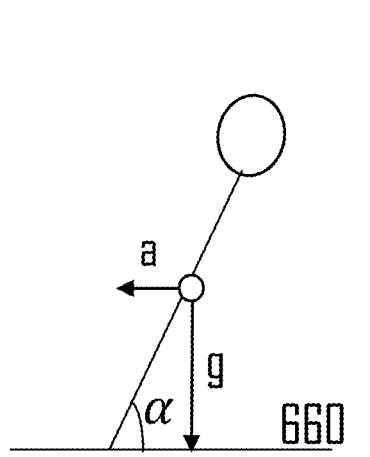
Figure 6F:
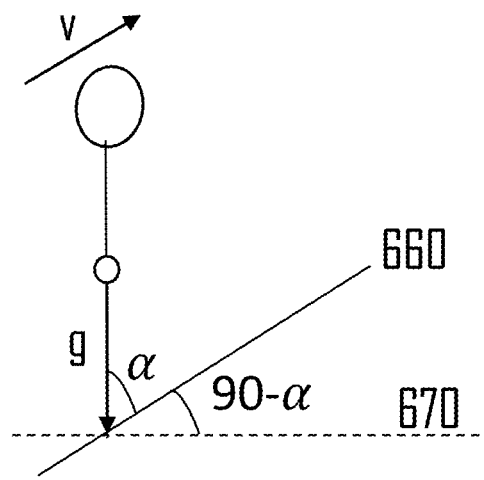

FIGS. 6D, 6E, and 6F illustrate some embodiments of obtaining the angle data discussed with respect to block 604. Referring to FIG. 6D, a user is shown to move uphill on a slope 650 having a certain angle β. User's speed v is indicated in the Figure with an arrow. So, in this example, the user may be moving uphill and the angle β may be angle of ascent. So, the angle data obtained in block 604 may comprise slope angle data indicating angle of a slope. The slope angle data may be obtained using measurements performed by one or more altimeters, barometers and/or one or more satellite positioning circuitries. For example, measuring altitude in point 652 and in point 654 (e.g. sampling frequency of 1 Hertz (Hz)) enables the apparatus 300 to determine the angle of ascent or descent (i.e. angle β of slope 650). The obtained angle β may be used in determining the energy consumption 630 according to the model of FIG. 6C.

According to an embodiment, with reference to FIGS. 6E and 6F, the apparatus 300 may obtain acceleration data on the user, wherein the angle data (i.e. obtained in block 604) comprises parameter α, wherein $$\alpha = \arctan\left(\frac{a}{g}\right),$$

α indicating acceleration of the user and g indicating gravitational acceleration (i.e. gravitational pull). Reference sign 660 may refer to the terrain surface (e.g. flat ground or slope). Parameter α may indicate angle between the body of the user and the surface 660.

Referring to FIG. 6E, the user may be accelerating, and thus the angle indicated or estimated by parameter α may be determined using both measured acceleration (i.e. a) and gravitational acceleration (i.e. g). Referring to FIG. 6F, the user may be running at a constant speed v, and thus there may be no component a. Hence, the parameter α may be calculated based on g. Reference sign 670 may indicate horizontal plane and reference sign 660 the surface which in this case may be a slope. The angle may thus be determined between the user and the slope 660.

In both examples (i.e. FIGS. 6E and 6F), the angle indicated by parameter α may be used in determining the energy consumption 630 according to the model of FIG. 6C.

Parameter α may be understood as an approximation of an angle that equals to a certain slope. That is, acceleration or deceleration by the user may be measured using, for example, satellite positioning circuitry (or more generally motion circuitry discussed above). This acceleration data may be used to determine the parameter α. So, although user may be running on flat ground, the parameter α may be calculated to obtain even better energy consumption estimate.

According to an embodiment, the apparatus 300 is configured to obtain a first energy consumption estimation for a predetermined distance at least on the basis of a predetermined model and the slope angle data (i.e. measured slope angle); obtain a second energy consumption estimation for the predetermined distance at least on the basis of a predetermined model and the parameter α (i.e. estimation of equivalent sloped caused by the acceleration); and obtaining the running power data based on both the first and second energy consumption estimates and the speed data. The predetermined model (e.g. shown in FIG. 6C) may be, for example, the cost of running discussed earlier. The first and second energy consumption estimates may be combined, e.g. summed together, to acquire a combined energy consumption estimate. The combined energy consumption estimate may then be multiplied with obtained speed (e.g. average speed or instantaneous speed) to obtain running power estimation (e.g. cost of running multiplied with speed outputs W/kg).

So, the apparatus 300 may calculate both angles α and β, and use both individually to determine first and second energy consumption estimates (e.g. based on the model of FIG. 6C) respectively, wherein the estimates in turn may be used to obtain the total or combined energy consumption estimation, for example. Then, the running power may be determined, by the apparatus 300, on the basis of the total energy consumption estimation and the obtained speed data. E.g. running power may be calculated by multiplying energy consumption estimation (e.g. how much energy is consumed per one meter), obtained using the model of FIG. 6C, with speed or velocity indicated by the speed data.

In another example embodiment, the apparatus 300 calculates angles α and β to obtain a combined angle or combined angle data (e.g. summing the angles α and β together). The combined angle may then be used to directly determine the combined energy consumption based on, for example, the model of FIG. 6C.

Figure 7A:
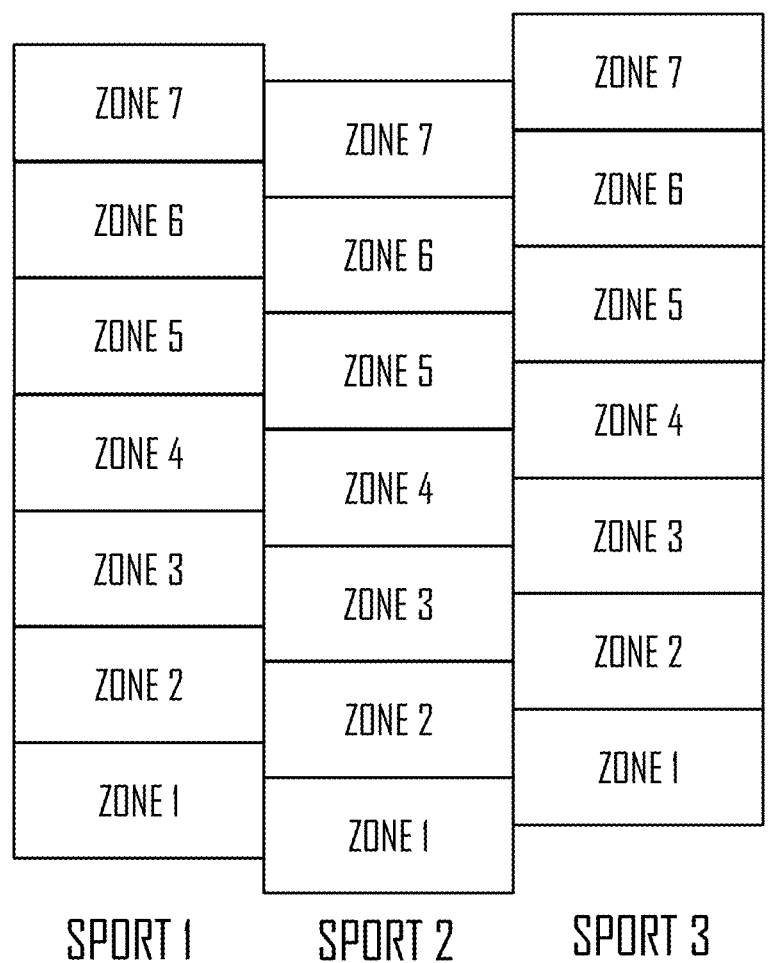
FIGS. 7A, 7B, 7C, and 7D illustrate some embodiments.

FIGS. 7A, 7B, 7C, and 7D illustrate some embodiments. Referring to FIG. 7A, the apparatus may classify the synthetic cardiac output power parameter in relation to a plurality of predetermined cardiac output power zones (e.g. zones 1-7). According to an embodiment, at least one predetermined cardiac output power zone is arranged for synthetic cardiac output power parameter values that represent cardiac output power exceeding a maximum heart rate of the user. For example, zones 6 and 7 may be used to indicate values that exceed the maximum heart rate. Indication about the current zone may be outputted to the user in real time during training, for example. In one example, the synthetic cardiac output power parameter indicates current heart rate zone or simply indicates that the synthetic cardiac output power parameter indicates values that exceed the maximum heart rate.

The cardiac output power zones may arranged, for example, such that zone 1 is for synthetic cardiac output power parameter values between 50 to 60% of maximum heart rate; zone 2 is for synthetic cardiac output power parameter values between 60 to 70% of maximum heart rate; zone 3 is for synthetic cardiac output power parameter values between 70 to 80% of maximum heart rate; zone 4 is for synthetic cardiac output power parameter values between 80 to 90% of maximum heart rate; zone 5 is for synthetic cardiac output power parameter values between 90 to 100% of maximum heart rate. Each zone may be associated with different exercise benefit. E.g. training on zone 1 may increase recovery, training on zone 2 may increase endurance, training on zone 3 may increase efficiency of blood circulation, training on zone 4 may increase speed endurance, and training on zone 5 may increase maximal performance. It is possible to use different number of zones. According to the present solution, at least one zone (e.g. zone 6 and zone 7) is arranged for synthetic cardiac output power parameter values which exceeds zone 5 or some other zone which upper limit is the maximum heart rate of the user. It may be beneficial to know that the training is on higher zones than the maximum heart rate as this may further give valuable information on how loading the training, which aims to increase maximal performance, is.

According to an embodiment, the cardiac output power zones are sport specific. Hence, for each sport (e.g. sport 1, sport 2, and sport 3) the zones may be different. Additionally, max heart rate may different between sports. For example, during swimming the body position and/or cold water may make user's heart rates generally lower compared with, for example, running or biking. So, basically the user may produce same or similar power output in different sports or conditions with different heart rates.

Figure 7B:
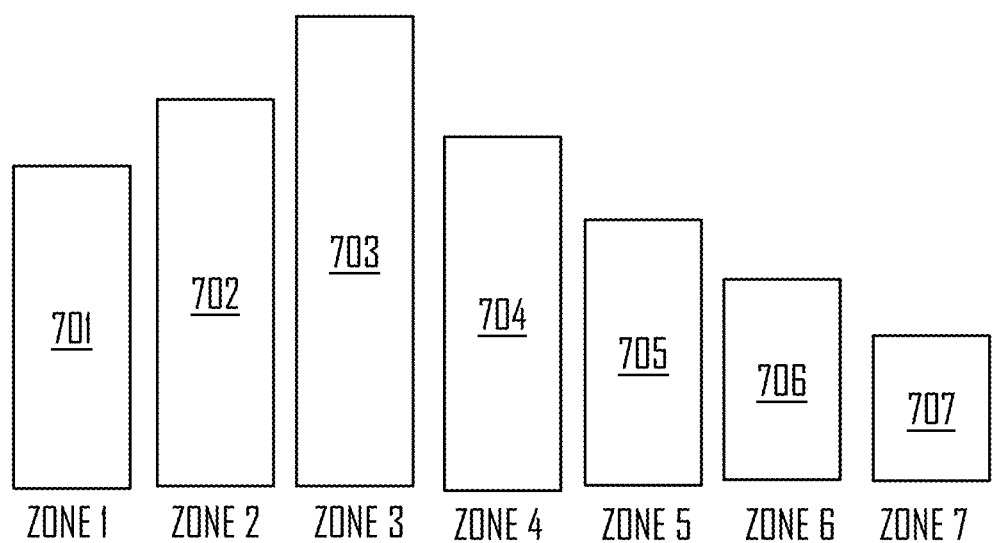

According to an embodiment, the apparatus 300 measures time spent on each zone (e.g. zones 1-7). This may enable the user to monitor how much time he/she has spent on each zone, as for example, the apparatus 300 may output said time measurements to the user, i.e. indicate time spent on each zone. For example, as shown in FIG. 7B, the time spent on each zone may be indicated with histogram 701-707. So, for example, if the synthetic cardiac output power parameter indicates value that is on zone 6, the apparatus 300 may increase timer associated with zone 6. Similar logic applies to all zones. So, the user may compare, regardless of performed sports, how much time he/she has trained on each zone (e.g. as shown in FIG. 7B).

According to an embodiment, all synthetic cardiac output power parameter values exceeding maximum heart rate are indicate with the same zone. Hence, using both zone 6 and 7 may not be necessary, for example.

Figure 7C:
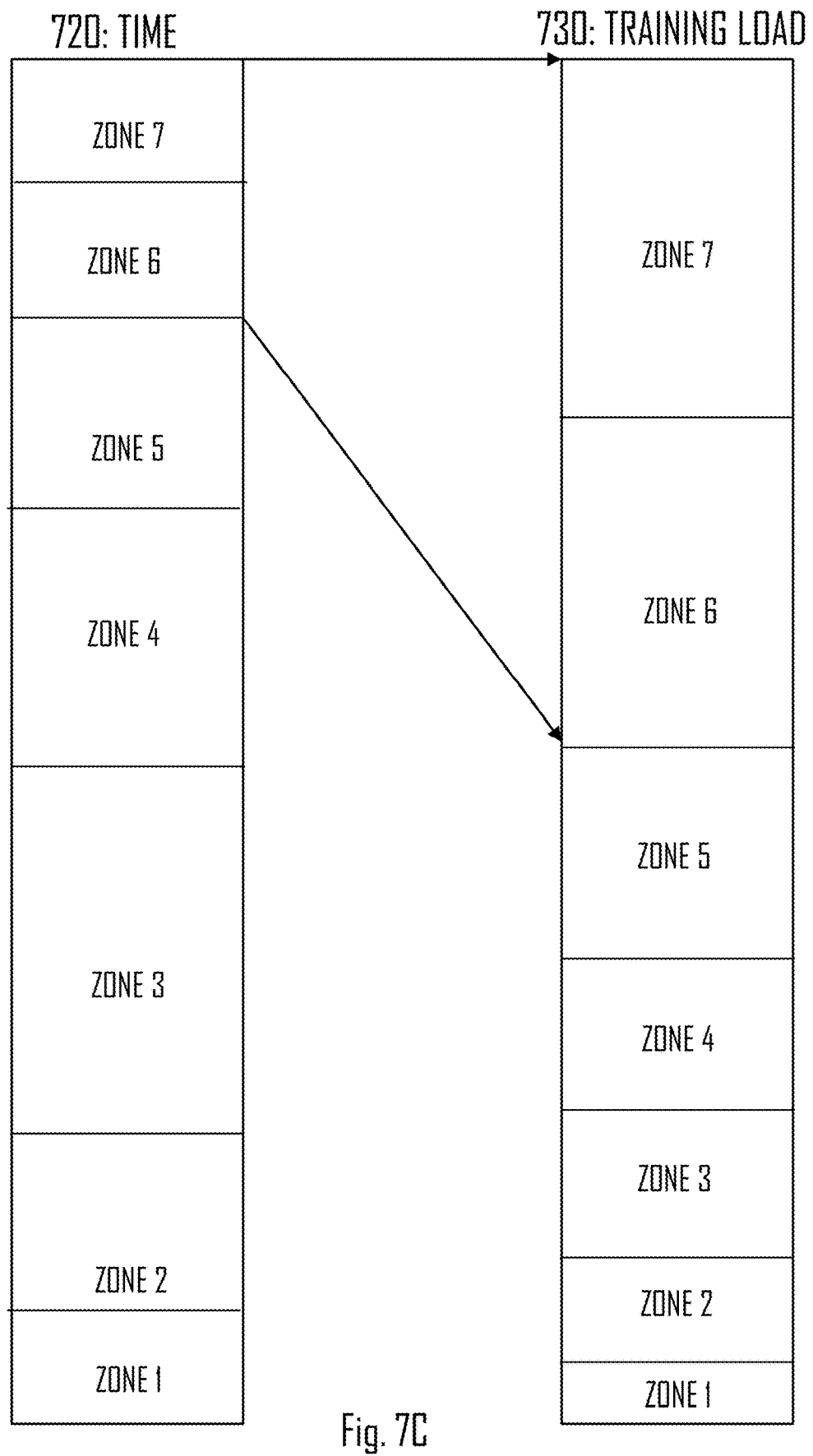

Referring to FIG. 7C, the time 720 spent on each zone (e.g. zones 1-7) is shown. According to an embodiment, the synthetic cardiac output power parameter is used, by the apparatus 300, to calculate training load, calorie consumption and/or training effect. In FIG. 7C, the time spent on higher zones may cause more training load 730 to the user. Use of training load 730 may further enhance the user's possibilities to monitor effect of different types of training. So, the higher the zone is, the higher the apparatus 300 estimates the training load 730 to be. This may be performed by utilizing, for example, a predetermined weighting scale: i.e. higher zones cause more training load, calorie consumption and/or training effect.

According to an embodiment, the apparatus 300 further determines cadence of the user based on the kinetic data comprising cadence data obtained using one or more motion sensors (e.g. motion circuitry); calculates a target cadence for obtaining a target cardiac output power zone amongst the plurality of predetermined cardiac output power zones (e.g. zones 1-7); and outputs an indication about the target cadence to the user. So, for example, the wrist device 102 may measure user's cadence (e.g. running cadence), and further determine that the synthetic cardiac output power parameter indicates values on a first zone. The user may have inputted a different target zone. The wrist device 102 may then determine how the cadence should be changed (e.g. increase or decrease) to acquire said target zone. The outputting the target cadence may comprise outputting the target cadence via audible and/or haptic indication.

According to an embodiment, at least one of the first threshold, the second threshold is different for a first type of physical exercise (e.g. sport 1) and for a second type of physical exercise (e.g. sport 2). For example, the maximum heart rate, anaerobic threshold and/or aerobic threshold may be different for each physical exercise. Hence, the zones (e.g. zones 1-7) may also differ as shown in FIG. 7A. Thus, the apparatus 300 may calculate a parameter, such as training load, calorie consumption and/or training effect based on the synthetic cardiac output power parameter for each physical exercise. This may enable, for example, training load to be compared between different physical exercises and/or combining training load of different exercises to acquire a combined training load. Same may apply to training effect and calorie consumption, for example.

Figure 7D:
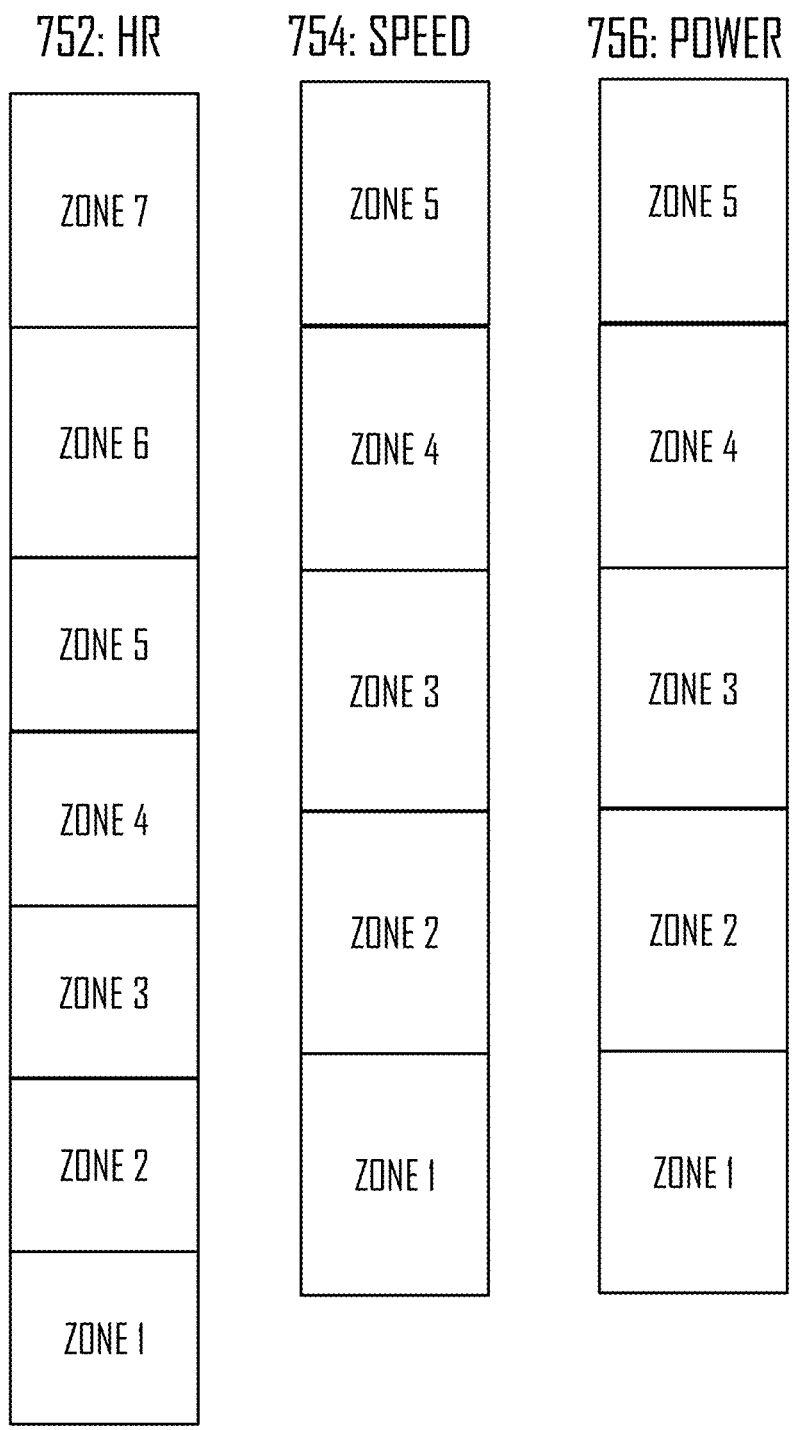

Referring to FIG. 7D, zones for heart rate 752, speed 754 and power output 756 are shown for a certain sport (e.g. running). Said zones may be obtained using one or more physiological tests performed on the user. For example, heart rate zone 5 may have an upper limit equaling to maximum heart rate of the user. This may be determined, on the basis of said tests, to equal to speed zone 3 and power zone 3 upper limits. Hence, zones 4 and 5 of speed and power may equal to synthetic cardiac output power parameter values that actually exceed the maximum heart rate. Hence, if speed and/or power (e.g. acquired as explained above) is situated on zone 4 or 5, the corresponding heart rate zone may be 6 or 7.

Figure 8A:
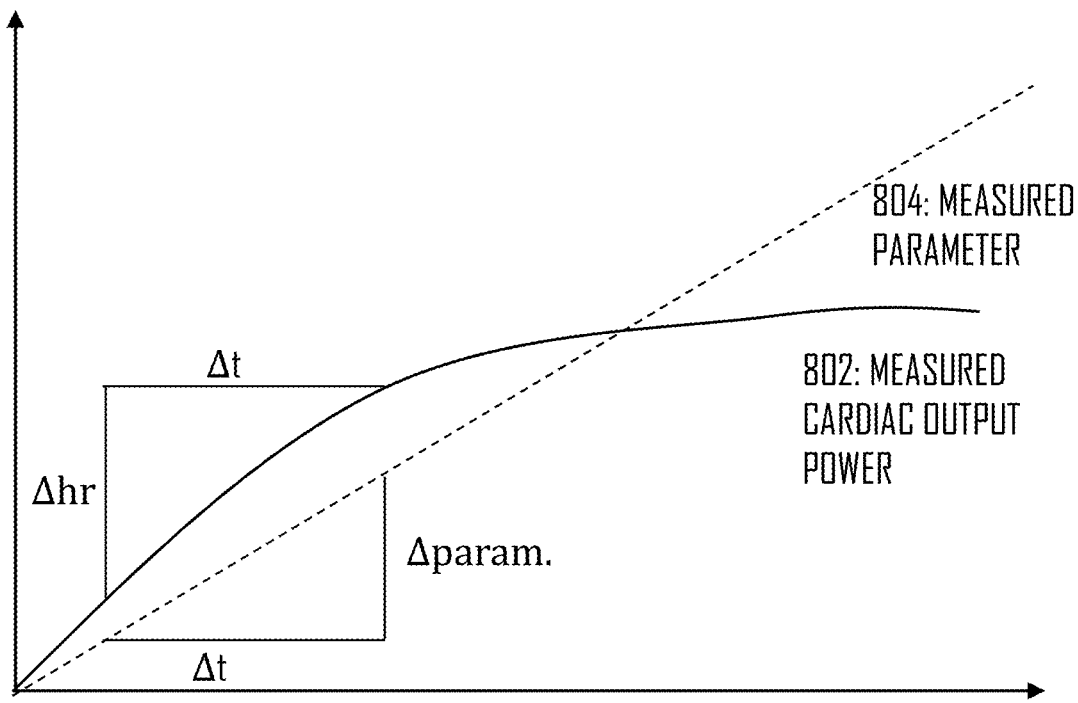
FIGS. 8A and 8B illustrate some embodiments.

In more general terms, the apparatus 300 may obtain test results from one or more physiological tests performed on the user; determine, based on the test result, a correspondence model between the cardiac output power of the user and at least one different measured test parameter (e.g. speed and/or power, such as running power); and utilize said correspondence model when determining the synthetic cardiac output power parameter. One example is shown in FIG. 8 illustrating an embodiment. Referring to FIG. 8A, said test parameter may be illustrated as measured parameter 804, which may be measured output power or speed, for example. Measured cardiac output power is shown with reference sign 802. The correspondence may be determined, for example, by calculating how much the measured cardiac output power 802 (e.g. heart rate) changes and how much the measured parameter 804 changes in same time. I.e. how much does an increase in the measured parameter 804 increase the measured cardiac output power. The correspondence model may be determined based on cardiac output power values that are below the first threshold, for example.

Still referring to FIG. 8A, according to an embodiment, a physiological test comprises increasing a target speed or target power as a function of time linearly or stepwise; ending the test in response to detecting that the user is unable to maintain the target speed or the target power; and measuring the cardiac output power 802 and said at least one different test parameter 804 during the test. As shown in FIG. 8A, the test may be used to determine the correspondence model between the parameter 804 and cardiac output power 802. Once the test has been performed and/or the correspondence model determined, the correspondence model may be used to estimate the synthetic cardiac output power parameter values on the basis of the measured parameter 804. It is possible to measure correspondence between the cardiac output power and more than one other parameter to further enhance the estimation.

The physiological test may be performed using one or more wearable devices. For example, the user may wear the wrist device 102 which may be configured to perform the test protocol of the physiological test. The wrist device 102 may thus be configured to measure the parameter 804 and the cardiac output power 802. The measurement may be performed solely with the wrist device 102 or additionally using one or more external sensors. The correspondence model may be determined or calculated by the wrist device 102 or by some external device using the data obtained during the test. For example, the wrist device 102 may measure kinetic data and/or power data on the user during the test, wherein the data may be used to obtain the parameter 804. The wrist device 102 may be configured to control the test by indicating to the user the target speed. For example, the target speed may be indicated to the user via user interface (e.g. audio or haptic feedback). One example of such may be to calculate target cadence on the basis of step length (e.g. running) and target speed, and indicate the target cadence to the user via the user interface of the wrist device 102. Another example of such may be to calculate target cadence on the basis of pedalling power (i.e. cycling) and target speed, and indicate the target cadence to the user via the user interface of the wrist device 102.

For example, by performing the physiological test in which the target speed is gradually or linearly increased, the correlation between heart rate 752 and speed 754 and/or power 756 may be determined by the apparatus 300 (see FIG. 7D). As described, the apparatus 300 may comprise the wrist device 102 and/or some other device, such as the server 114.

In an embodiment, said physiological test refers to running test. Based the running test, the zones shown in FIG. 7D may be determined, for example. For example, HR's 752 zone 5 upper limit may equal to maximum heart rate, wherein the maximum heart rate may further indicate VO2 maximum of the user. Maximum heart rate may further indicate maximum aerobic speed (MAS). MAS may equal to zone 3 of speed 754, for example. Lower limit of zone 1 of speed 754 and zone 1 of power 756 may equal to walk-to-run transition speed (W2RS). Hence, by performing the running test using the wrist device 102, the VO2 max, W2RS and/or MAS may be determined. These parameters may further be used to determine the zones for HR 752, speed 754 and power 756.

So, basically once the correspondence model has been determined, the apparatus 300 may obtain measurements on said other parameter 804, and determine the synthetic cardiac output power parameter on the basis of said parameter 804 (or parameters) and the correspondence model. Hence, it may not be even necessary to measure cardiac output power anymore once the correspondence model has been determined. However, it may still be beneficial to more accurately determine when the first threshold is exceeded, for example. Further, the measured cardiac output power may be used, i.e. displayed or the synthetic cardiac output power parameter determined on the basis of the measured cardiac output power, before or prior to the exceeding the first threshold.

Figure 8B:
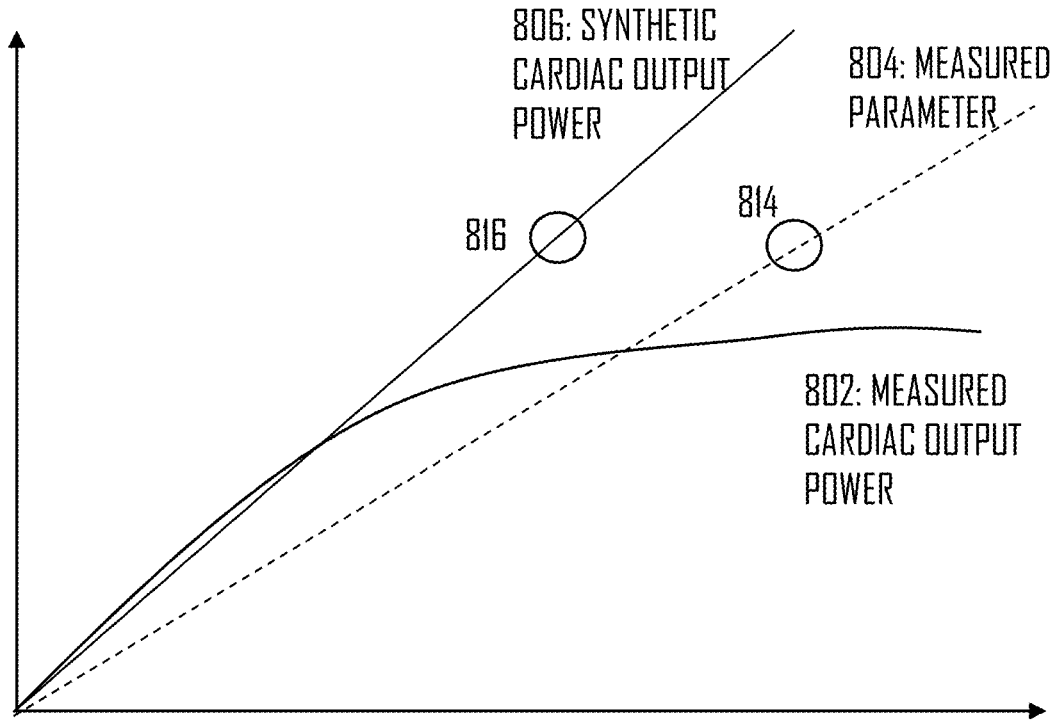

FIG. 8B illustrates an embodiment. Referring to FIG. 8B, the synthetic cardiac output power parameter 806 is determined based on the correspondence model and at least one value 814 of said at least one measured test parameter 804. For example, in the specific example, value 816 of the synthetic cardiac output power parameter is determined on the basis of the correspondence model (e.g. FIG. 8A) and the value 814 of the measured parameter 804. For example, the correspondence model may indicate linear correlation between the synthetic cardiac output power parameter 806 and the measured parameter 804. However, it may be possible to use or determine different kinds of correlations. Basically, the determined correlation model may be used to extrapolate the cardiac output power values (e.g. heart rate) to indicate values which exceed the maximum heart rate. The synthetic cardiac output power parameter 806 may be used to indicate these extrapolated values. However, and as discussed, the synthetic cardiac output power parameter may in some cases also indicate values which are less than maximum heart rate (e.g. real measured heart rate or extrapolated values which not exceed the maximum heart rate).

According to an example embodiment, speed or velocity as used above refers to flat equivalent speed or velocity. For example, if a user is running uphill with a certain speed, the flat equivalent speed may be determined on the basis of said measured speed and a measured angle of ascent. For example, running with a certain speed uphill on a slope having 5% elevation may equal to certain flat equivalent speed meaning equivalent speed on flat ground, e.g. race track, (i.e. elevation 0%).

According to an example embodiment, the flat equivalent speed is calculated based on obtaining flat ground cost of running or walking (i.e. calculating cost of running or walking with the assumption that slope angle is 0 although it would be something else, and obtaining cost of running or walking taking into account the slope angle. Thus, flat equivalent speed would then be, for example, cost of running (measured angle)/cost of running (flat) multiplied by measured speed. Although cost of running is used as an example, some other predetermined model, such as cost of walking, may additionally/alternatively be used.

According to yet another embodiment, the apparatus 300 is configured to obtain speed data based at least on the kinetic data on the user. That is, the motion circuitry may be used to measure the kinetic data on the user, and from the kinetic data various parameters may be calculated, one being speed or velocity. The apparatus 300 may use said speed data as a basis for determining the synthetic cardiac output power parameter.

According to yet another embodiment, the apparatus 300 utilizes both speed data and power data as a basis for determining the synthetic cardiac output power parameter. Example of this may be shown in FIG. 7D, for example.

According to an embodiment, the first threshold equals to resting heart rate of the user. Hence, the synthetic cardiac output power parameter may be used to indicate user's heart activity instead of actual measured heart activity. For example, if the correspondence model between another parameter (e.g. parameter 804) and heart rate is determined, the apparatus 300 may output the synthetic cardiac output power based on measuring said another parameter. That is, certain power, speed, and/or slope angle may be determined to equal to a certain cardiac output power. Although such determination may not be as accurate as actually measuring the heart rate, the determination may give valuable information to the user in cases where she/he does not have a heart rate monitor at her/his disposal.

According to an embodiment, physical exercise discussed above comprises at least one of the following: running, jogging, swimming, cycling, mountain biking, climbing, team sport activity, (such as football, soccer, rugby to name a few examples), and Nordic skiing (e.g. cross-country skiing).

According to an example embodiment, the running power is determined on the basis of measurements by the wrist device 102. Additionally or alternatively, one or more external sensors configured to be placed on one or more different locations on the user body may be used. For example, a sensor or sensors may be placed in the front, back or side of the torso/waist, embedded in shoes, attached to wrist, arm, leg or ankle, or attached to head. These various implementations have various advantages, such as convenience to the user, accuracy of speed or position, accuracy of measuring running/walking technique, sensor data quality. Furthermore, as power equals force multiplied by speed or velocity, running power can also be detected, for example, by detecting the force with shoe insoles (e.g. force sensor(s) at shoes or insoles) and velocity by motion sensors (e.g. accelerometer and/or satellite positioning circuitry). As yet another example, it is possible to measure 3D acceleration (for example by a sensor in chest strap) and use that in determining running power (Power=Force×velocity; Force=mass×acceleration). Force may be measured, for example, using a force-plate(s) on a treadmill or shoe insole sensor(s).

According to an example embodiment, energy expenditure calculation (e.g. energy consumption estimate) is based purely on accelerometer data. For example, the so called Accelerometry-Based Mean Amplitude Deviation (MAD) may be used. As explained above, energy expenditure and output power may correlate with each other.

According to an example embodiment, running power is determined, by the apparatus 300, by measuring and/or obtaining force data on the user using a force sensor at shoe insole(s), force plate(s) and/or using an inertial sensor(s). Said force data may represent supporting force. The apparatus may further measure kinetic and potential energy change based at least on the force data obtained on the user. Said change may further be used to calculate running power of the user. It is noted that definition of running power may change per implementation. However, at least some workable examples are disclosed in the embodiments and examples above.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the functionalities according to any one of the embodiments or operations thereof may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, person interface, display circuitry, person interface circuitry, person interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory and/or transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A method for monitoring physical exercise performance, the method comprising:
   obtaining, by utilizing measurements performed by one or more cardiac activity sensors, cardiac output power data on a user;
   obtaining, by utilizing measurements performed by one or more sensors, speed data and angle data on a route of the user, the speed data and angle data characterizing physical exercise intensity of the physical exercise performed by the user;
   obtaining an energy consumption estimation for a predetermined distance at least on the basis of a predetermined model and the angle data;
   obtaining running power data at least based on the energy consumption estimation and the speed data;
   detecting that a measured cardiac output power exceeds a first threshold or that physical exercise intensity changes according to a rate exceeding a second threshold;
   upon said detecting, determining a synthetic cardiac output power parameter based at least partly on the running power data; and
   outputting the synthetic cardiac output power parameter.

2. The method of claim 1, further comprising determining the synthetic cardiac output power parameter based on the cardiac output power data before the detecting that the measured cardiac output power exceeds the first threshold or that the physical exercise intensity changes according to a rate exceeding the second threshold.

3. The method of claim 1, wherein the first threshold equals a cardiac output power value corresponding to an anaerobic threshold of the user.

4. The method of claim 1, wherein the first threshold equals a cardiac output power value corresponding to a maximum heart rate of the user.

5. The method of claim 1, wherein the cardiac output power represents a heart rate parameter.

6. The method of claim 1, wherein the outputted synthetic cardiac output power parameter indicates a value that is greater than a maximum heart rate of the user.

7. The method of claim 1, wherein at least one of the first threshold, the second threshold is different for a first type of physical exercise and for a second type of physical exercise.

8. The method of claim 1, further comprising:
   classifying the synthetic cardiac output power parameter in relation to a plurality of predetermined cardiac output power zones, at least one predetermined cardiac output power zone arranged for synthetic cardiac output power parameter values that represent cardiac output power exceeding a maximum heart rate of the user.

9. The method of claim 8, further comprising:
   determining cadence of the user based on the running power data comprising cadence data obtained using one or more motion sensors;
   calculating a target cadence for obtaining a target cardiac output power zone amongst the plurality of predetermined cardiac output power zones; and
   outputting an indication about the target cadence to the user.

10. The method of claim 1, further comprising:
    obtaining physical exercise power data based at least on the running power data; and
    determining the synthetic cardiac output power parameter based at least partly on the physical exercise power data.

11. The method of claim 1, wherein the angle data comprises slope angle data obtained using a barometer.

12. The method of claim 1, further comprising: obtaining acceleration data on the user,
    wherein the angle data comprises parameter $\alpha$, wherein $$\alpha = \arctan\left(\frac{a}{g}\right),$$

a indicating acceleration of the user and g indicating gravitational acceleration.

13. The method of claim 12, further comprising:
    obtaining a first energy consumption estimation for a predetermined distance at least on the basis of a first predetermined model and the slope angle data;
    obtaining a second energy consumption estimation for the predetermined distance at least on the basis of a second predetermined model and the parameter $\alpha$; and
    obtaining the running power data based on both the first and second energy consumption estimates and the speed data.

14. The method of claim 1, further comprising:
    obtaining test results from one or more physiological tests performed on the user;
    determining, based on the test result, a correspondence model between the cardiac output power of the user and at least one different measured test parameter; and
    utilizing said correspondence model when determining the synthetic cardiac output power parameter.

15. The method of claim 14, wherein the synthetic cardiac output power parameter is determined based on the correspondence model and at least one value of said at least one different measured test parameter.

16. The method of claim 14, wherein the physiological test comprises:
    increasing a target speed as a function of time linearly or stepwise;
    ending the test in response to detecting that the user is unable to maintain the target speed; and
    measuring the cardiac output power and said at least one different test parameter during the test.

17. The method of claim 1, further comprising:
    obtaining the speed data based at least on the running power data; and
    determining the synthetic cardiac output power parameter based at least partly on the speed data.

18. An apparatus for monitoring physical exercise performance, the apparatus comprising:
    at least one processor; and
    at least one memory including a computer program code, wherein the at least one memory and the computer program code are configured, with the at least one processor, to cause the apparatus to perform operations comprising:
    obtaining, by utilizing measurements adapted to be performed by one or more cardiac activity sensors, cardiac output power data on a user;
    obtaining, by utilizing measurements adapted to be performed by one or more sensors, speed data and angle data on a route of the user, the speed data and angle data characterizing physical exercise intensity of the physical exercise performed by the user;
    obtaining an energy consumption estimation for a predetermined distance at least on the basis of a predetermined model and the angle data;

obtaining running power data at least based on the energy consumption estimation and the speed data;

detecting that a measured cardiac output power exceeds a first threshold or that physical exercise intensity changes according to a rate exceeding a second threshold;

upon said detecting, determining a synthetic cardiac output power parameter based at least partly on the running power data; and outputting the synthetic cardiac output power parameter.

19. A computer program product embodied on a distribution medium readable by a computer and comprising program instructions which, when executed by an apparatus, cause the apparatus at least to perform a method comprising:

obtaining, by utilizing measurements performed by one or more cardiac activity sensors, cardiac output power data on a user;

obtaining, by utilizing measurements performed by one or more sensors, speed data and angle data on a route of the user, the speed data and angle data characterizing physical exercise intensity of the physical exercise performed by the user;

obtaining an energy consumption estimation for a predetermined distance at least on the basis of a predetermined model and the angle data;

obtaining running power data at least based on the energy consumption estimation and the speed data;

detecting that a measured cardiac output power exceeds a first threshold or that physical exercise intensity changes according to a rate exceeding a second threshold;

upon said detecting, determining a synthetic cardiac output power parameter based at least partly on the running power data; and outputting the synthetic cardiac output power parameter.

\* \* \* \* \*